United States Patent [19]

Ishiguro et al.

[11] Patent Number: 4,997,829
[45] Date of Patent: Mar. 5, 1991

[54] PENEM COMPOUNDS, AND USE THEREOF

[75] Inventors: Masaji Ishiguro; Hiromitsu Iwata; Takashi Nakatsuka, all of Mishima, Japan

[73] Assignee: Suntory Limited, Osaka, Japan

[21] Appl. No.: 496,145

[22] Filed: Mar. 9, 1990

Related U.S. Application Data

[63] Continuation of Ser. No. 315,232, Feb. 23, 1989, abandoned, which is a continuation of Ser. No. 837,593, Mar. 7, 1986, abandoned.

[30] Foreign Application Priority Data

Mar. 9, 1985 [JP] Japan .................................. 60-47103

[51] Int. Cl.$^5$ .................. C07D 499/00; A61K 31/425
[52] U.S. Cl. ..................................... 514/192; 514/195; 540/310
[58] Field of Search ................. 540/310; 514/192, 195

[56] References Cited

U.S. PATENT DOCUMENTS 4,260,618 4/1981 Christensen et al. ............... 424/263
4,272,437 6/1981 Menard ............................... 540/310

Primary Examiner—Nicholas S. Rizzo
Attorney, Agent, or Firm—Burgess, Ryan & Wayne

[57] ABSTRACT

A penem compound represented by the general formula:

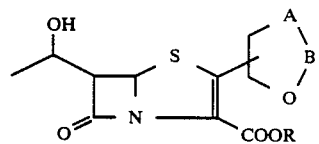

(wherein R denotes hydrogen or allyl group, A denotes oxygen atom or methylene group and B denotes methylene, ethylene or carbonyl group) or a pharmacologically acceptable salt is produced through several processes.

The compound exhibits stronger activities against wide variety of gram-positive and gram-negative bacteria as compared with known penem compounds.

16 Claims, No Drawings

PENEM COMPOUNDS, AND USE THEREOF

This application is a continuation of application Ser. No. 315,232, filed 2/23/89, which is a continuation of U.S. Pat. No. 837,593 filed 3/7/86, both now abandoned.

The present invention relates to a compound represented by the general formula:

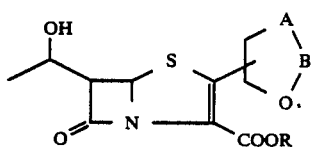

(wherein R denotes hydrogen or allyl group, A denotes oxygen or methylene group, and B denotes methylene, ethylene or carbonyl group) or a pharmacologically acceptable salt thereof.

The present compounds represented by the above general formula (1) are novel and have very remarkable effect in treatment for infections with gram-positive and gram-negative bacteria and can be utilized broadly as medicines for human as well as animals.

It is well known that many kinds of antibiotics have been invented and employed since the invention of penicillin by Fleming and the employment of penicillin as a chemotherapeutic agent by Florey.

In the field of antibiotics in Japan, those most widely employed are β-lactam compounds which account for not less then 80% of the whole antibiotics employed.

The reasons why the β-lactam antibiotics are widely employed are the strongness of antibacterial activity and the broadness of antibacterial spectrum as well as high safety of the antibiotics, and a further reason is that they can be obtained by fermentation.

In the β-lactam agent produced by microorganisms, there are penicillins, cephalosporins, nocardicins, clavulanic acid, carbapenems etc. Many carbapenem compounds have been already produced by fermenting Actinomycetes or Bacteria, however, penem compounds have unnatural type of β-lactam and have not yet been found in natural sources.

Penem skeleton corresponds to that wherein the methylene group at 1-positon of carbapenem skeleton is replaced by sulfur atom as shown in the following formula;

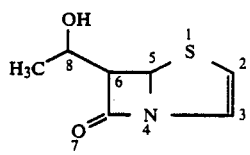

and both skeletons have very analogous structures. The penam skeleton of penicillin has great strain in the ring. While the stability of cephem skeleton in cephalosporins is hindered by the double bond in the six-membered ring so that it reacts with transpeptidase to inhibit the enzyme's activity. From the reasons mentioned above strong activity was expected of penem skeleton too. In fact, strong activity has been found in 1-thiathienamycin [S.OHYA et al., Antimicrob. Agents Chemother., 21, 492, (1982) and Sch 29482 (A. K. Ganguly et al., J. Antimicrob. Chemother., (Suppl. C) 9, 1 (1982)] etc.

As mentioned in the foregoing, many penem compounds have been synthesized from the reasons such as similarlity in skeleton with penicillin. For example, there can be exemplified Japanese Patent Application Disclosure Nos. 119486/1979, 88291/1979, 25110/1981, 9784/1982 etc.

As to the synthesis of these penem compounds, there have been many reports, for example, A. Longo et al. [Gazz. Chim. Ital., 111, 371-77, (1981)], V. M. Girijavallabhan et al. [Tetrahedron Letters, 22, 3485 (1981)].

Thinking about to develope new antibiotics, the present inventors set their sight on β-lactam antibiotics.

Among β-lactam antibiotics, penem compounds are generally chemically stable and more stable than carbapenem to kidney dehydropeptidase I, although there are still many unobvious points in their biological evaluation.

The present inventors have conducted research to find out penem compounds which have, besides the advantages mentioned above, strong activities to the broad range of gram-positive and gram-negative bacteria and can be employed even orally, and came to establish the present invention. Furthermore, as a part of the above research, the present inventors have carried out many improvements in the synthesis method to produce penem compounds more cheaply.

The present invention is directed to a penem compound represented by the general formula:

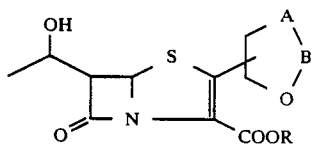

(wherein R denotes hydrogen or allyl group, A denotes oxygen or methylene group, and B denotes methylene, ethylene or carbonyl group) or a pharmacologically acceptable salt thereof.

The penem compound represented by the above general formula (1) can be synthesized by the following methods.

Firstly, there is described a production method of azetidinone compound (2) which is the precursor for producing the penem compound.

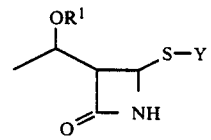

(wherein $R^1$ denotes the protective group of hydroxyl group, Y denotes a substituted or unsubstituted phenyl group).

A butylsulfide which can be represented by the general formula (3),

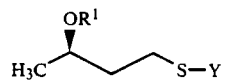

(wherein $R^1$ and Y denote the same definitions as above), is described as dl-form in the references of H. A. Khan et al., Tetrahedron Letters, 23, 5983 (1982); Y.

Ueno et al., Bull. Chem. Soc. Jpn., 53, 3675 (1980); and P. Loiseau at al., Pharm. Acta. Helv., 58, 115 (1983), and can be synthesized from the raw material, 3(R)-1,3-butanediol. The compound of the formula (3) is chlorinated by N chlorosuccinimide or sulfuryl chloride etc. to produce a compound of the general formula,

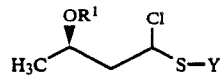

(wherein R¹ and Y denote the same definitions as above) and then treating with a chloride or carbonate of alkali metal, or an alkali metal alkoxide to obtain a compound of the general formula,

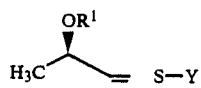

(wherein R¹ and Y denote the same definitions as above).

The above dehydrogen-chloride reaction is carried out preferably under heating. The compound of the formula (5) can also be obtained by reacting the butylsulfide of the formula (3) with an oxidizing agent such as m-chloroperbenzoic acid, hydrogen peroxide, perbenzoic acid, peracetic acid etc. to covert to a sulfoxide represented by the general formula (6),

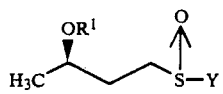

(wherein R¹ and Y denote the same definitions as above) and then heating in a solvent.

The compound of the formula (5) thus obtained is a mixture of cis- and trans-forms to the double bond, however, separation to each form from the mixture is unnecessary to convert to an azetidinone compound of the formula (2).

The azetidinone compound can be obtained by reacting the compound of the formula (5) with chlorosulfonylisocyanate in a solvent such as an ether or a chlorinated hydrocarbon, and then treating with thiophenol and pyridine. There are two isomers, namely 1′R, 3S, 4R isomer (2a) and 1′R,3R,4S isomer (2b), in the azetidinone compound.

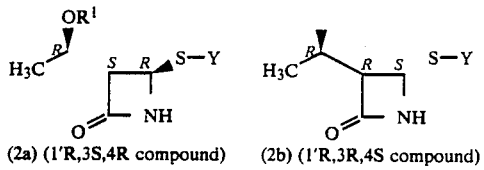

(2a) (1′R,3S,4R compound)    (2b) (1′R,3R,4S compound)

The former isomer has the same steric configuration as thienamycin. The separation of two isomers can be carried out very easily by recrystallization.

It is obvious for a specialist that optically inactive azetidinone compound (2) can be obtained by the same procedures employing optically inactive 1,3-butanediol instead of 3(R)-1,3-butanediol.

The production method of the present penem compound (1) is described in the following:

An azetidinone compound of the above general formula (2) is easily converted to sulfonyl compound (7) by oxydation.

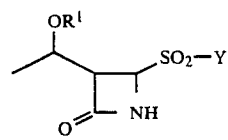

(wherein R¹ and Y denote the same definitions as above)

It is known that the functional groups at 4-positions of the compound (7) and an azetidinone compound represented by the general formula (8),

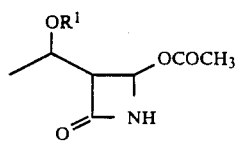

(wherein R¹ denotes the same definition as above) can be replaced with thiocarbonic acid (Japanese Patent Application Disclosure No. 25110/1981).

Starting from the compound (7) or (8), the penem compound (1) can be produced by the procedures illustrated in the following:

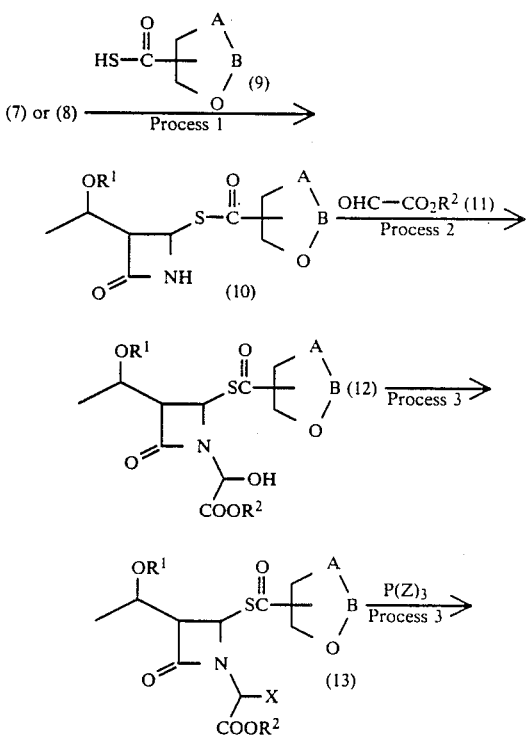

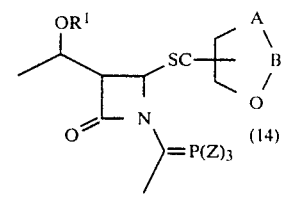

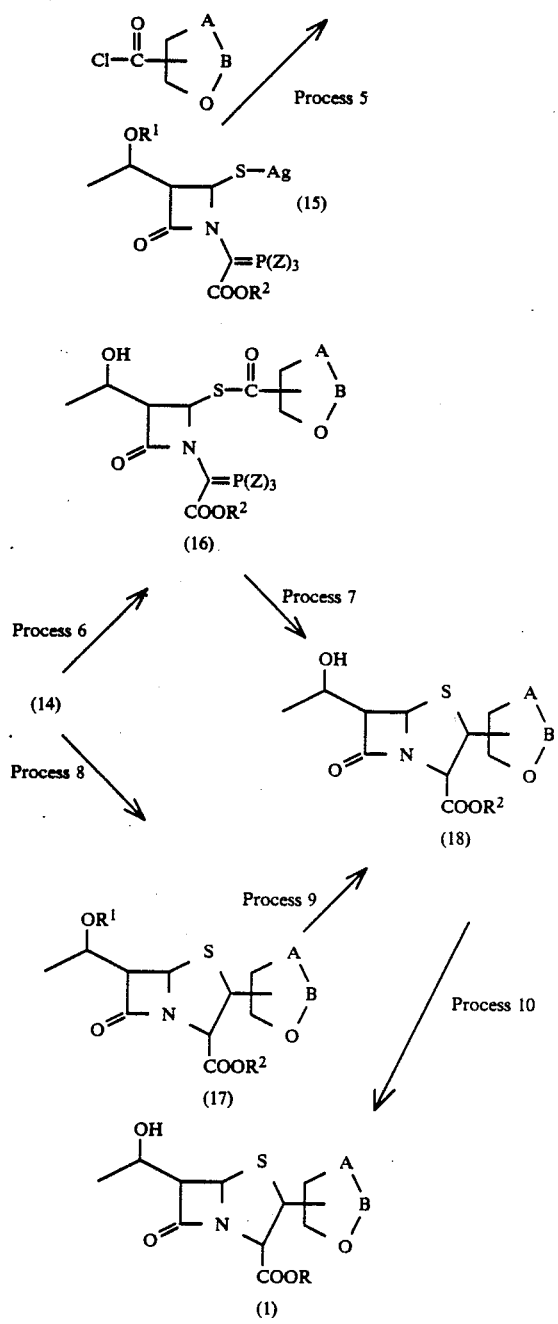

(wherein R, R¹ and

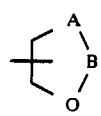

denote the same definitions as above, R² denotes the protective group of carbonyl group, X denotes a halogen and Z denotes aryl group)

Concrete groups denoted by the formula of

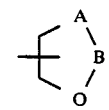

are exemplified as follows;

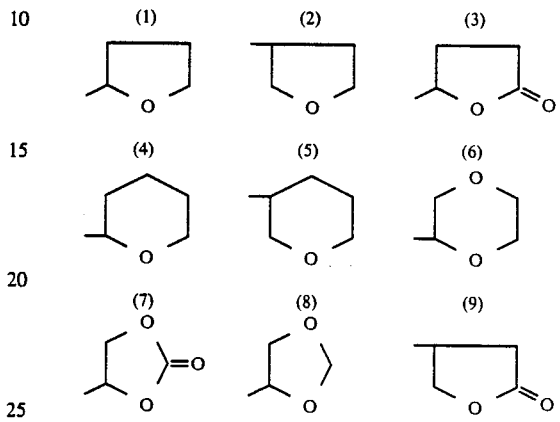

In the compounds represented by the above mentioned general formula (1), there are optical and steric isomers owing to the assymmetric carbons, though all of them are shown by a plane formula, but the scope of the present invention is not limited by the plane formula. However, a compound wherein the carbon atom at 5-positon of the penem skeleton has R configuration and the carbon atom at 6-position has S configuration can be selected. With regard to 1-hydroxyethyl group, a substituent at 6-position, R configuration is preferable and with regard to a substituent at 2-position, a substituent wherein the carbon atom at -position has R configuration is preferably selected. the above-mentioned processes are explained in order in the following:

The first process is that of obtaining a thiocarboxylic acid ester of the general formula (10) wherein the reaction is proceeded by adding an alkali metal hydroxide such as sodium hydroxide, potassium hydroxide etc. or an alkali metal alkoxide such as sodium methoxide, sodium ethoxide to an azetidinone compound of the general formula (7) or (8) and 1.5 to 2 equivalent of a thiocarbonic acid represented by the general formula (9) in a solvent such as water and an alcohol such as methanol, ethanol etc., a ketone such as acetone, methyl ethyl ketone etc. or an ether such as tetrahydrofuran, dioxane etc. to adjust the pH of the solution 8 to 10. After the reaction is completed, the mixture is neutralized with diluted mineral acid and extracted with a water-immiscible solvent, followed by washing the organic layer with water. After the organic layer is dried with a drying agent, organic solvent in the layer is distilled off to obtain the desired compound (10). Some of the desired compounds thus obtained may be employed in the next process without purification, however, the compounds can be purified further by column chromatography, preparative thin layer chromatography, recrystallization etc.

The second process is that of producing a N-hydroxyl ester compound of the general formula (12) wherein the desired adduct compound of the general formula (12) is obtained by heating and refluxing a compound of the general formula (10) with a glyoxylic acid ester of the general formula (11) in an ether such as tetrahydrofuran, dioxane etc. or an aromatic hydrocarbon such as benzene, toluene, and xylene. The product of this process can be obtained by distilling off solvent from the reaction mixture, and, in many cases, can be employed without further purification in the next process, however, as the case may be, can be purified by column chromatography, recrystallization etc.

The third process is that of producing the compound of the general formula (13) by halogenation. In carrying out the reaction of this process, the reaction is accomplished by diluting the compound of the general formula (12) with an organic solvent and contacting with a thionyl halide such as thionyl chloride and thionyl bromide, a phosphorus oxyhalide such as phosphorus oxychlorride, or a phosphorus halide represented by phosphorus petachloride in the presence of a base. In this process, preferable temperature is −40° C. to 0° C. and the reaction is completed within several hours.

As a base employed in this process, an organic base such as triehtylamine, diiosopropylethylamine, pyridine or lutidine is preferable. As the solvent, a solvent not relevant to the reaction may be employed, however, preferable solvent is an ether such as tetrahydrofuran or dioxane, or a hydrocarbon chlaride such as methylene chloride, chloroform etc.

The product of this process may be obtained in the following manner:

After the reaction is completed, the mixture is diluted with an organic solvent immiscible with water, washed with saturated aqueous solution of sodium hydrogen carbonate and then water, dried with a drying agent, and solvent is distilled off.

The product can be employed without further purification in the next proces, however, it may be purified by a purification means such as recrystallization, column chromatography, preparative thin layer chromatography etc. As the case may be, the product may be employed in the next process as such an unpurified material obtained by filtering off insoluble materials from the reaction mixture after the reaction is completed, and concentrating the filtrate.

The fourth process is that of producing a phosphorusilide compound of the formula (14).

In carrying out the reaction of this process, the compound of the general formula (13) is mixed with an organic solvent and treated with a triarylphosphine such as triphenylphosphine etc. in the presence of a base. The reaction temperature may usually be room temperature to 100° C. As the base employed, an organic base such as triethylamine, diisopropylethylamine, lutidine etc. is preferable and as the solvent, an ether such as tetrahydrofuran, dioxane etc., an aromatic hydrocarbon such as benzene, toluene etc. and an aliphatic hydrocarbon such as cyclohexane is preferable.

After the reaction is finished, the reaction mixture is washed with an aqueous diluted acid, diluted alkali and water in order, dried with a drying agent, and then concentrated to obtain the product compound (14). The product thus obtained may be purified by a purification means such as column chromatography, recrystallization, preparative thin layer chromatography etc., if desired.

While, the desired compound of the general formula (14) can be obtained by admixing the known compound of the general formula (15) [Japanese Patent Application Disclosure No. 25110/1981] with an acid chloride of the general formula

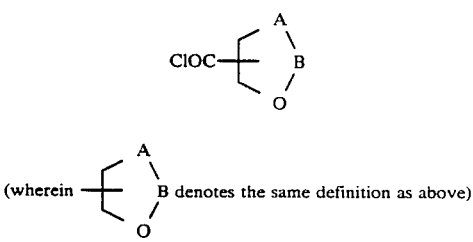

(wherein denotes the same definition as above)

in a solvent of hydrocarbon chloride such as methylene chloride, chloroform etc., or an aromatic hydrocarbon such as benzene, toluene, xylene etc.

In carrying out this fifth process, preferable reaction temperature is usually from 0° C. to room temperature and the reaction is completed within 5 hours. After the reaction is completed, insoluble materials (mainly an Ag salt) in the reaction mixture are filtered off, the filtrate is washed with water and dried with a drying agent, and then concentrated to obtain the aimed compound (14).

The product (14) thus obtained can be purified by purification means shown in the process (4).

The sixth process is that of producing the compound of the general formula (16).

The procedure for removing a protective group of hydroxyl group in this process varies depending on the property of the protective group. For example, when a silyl group such as t-butyldimethylsilyl group is employed as the protective group, the compound of the general formula (14) is diluted with a solvent and contacted with tetrabutylammonium fluoride, whereby the reaction proceeds easily. The reaction temperature may be around room temperature and the solvent employed is preferably an organic solvent belonging to an ether such as dioxane, tetrahydrofuran etc.

After the reaction is completed, the reaction mixture is diluted with an organic solvent immiscible with water, washed with saturated aqueous solution of sodium carbonate and then water, dried with a drying agnet, and concentrated to obtain the desired compound (16). The compound (16) can be employed as it is in the next process, however, it may be purified by a purification means such as column chromatography, recrystallization, preparative thin layer chromatography etc., if necessary.

The seventh process is that of producing a penem compound of the general formula (18), wherein a compound of the general formula (16) is heated in a solvent to subject to a ring-closure reaction.

In carrying out this process, the solvent employed is not limited particularly, however, a solvent of an aromatic hydrocarbon such as benzene, toluene, xylene etc. and an ether such as dioxane, diethoxyethane etc. is preferable.

After the reaction is completed, solvent is distilled off from the reaction mixture, whereby the desired compound of this process can be obtained. The compound (18) thus obtained can further be purified by column chromatography or recrystallization, if necessary.

The eighth process is that of producing a penem compound of the general formula (17), wherein a phoshorusilide compound of the general formula (14) is heated and subjected to a ring-closure reaction in the same manner as in the seventh process.

This process is similarly to the seventh process and after the reaction is completed, the reaction mixture is concentrated, whereby the aimed compound (17) can be obtained. The compound thus obtained can be purified by a conventional means such as column chromatography, recrystallization, preparative thin layer chromatography etc., if necessary.

The nineth process is that of producing a penem compound of the previously mentioned general formula (18).

This process can be carried out in the same manner as in the sixth process mentioned above. The product of the nineth process can be purified similarly to the sixth process by a conventional purifying means, for example, column chromatography, recrystallization, preparative thin layer chromatography etc.

The tenth process is that of producing a penem compound of a general formula (1), wherein the protective group of carboxyl group in the penem compound of the general formula (18) is removed.

The procedure for removing the protective group varies depending on the species of the group, however, it can be removed by known procedures in this field of art.

In the case that the protective group is an aralkyl group such as benzyl, p-nitrobenzyl etc., there may preferably be exemplified a procedure wherein hydrogen and a catalyst for catalitic reduction such as palladium-carbon or an alkali metal sulfide is reacted with the compound (18).

In the case that the protective group is allyl group, there can be exemplified a procedure employing trialkylphosphine or palladium tetrakistriarylphosphine and a procedure employing palladium tetrakisarylphosphine or tributyltin hydride.

The reaction is carried out in the presence of a solvent which is not limited particularly, if it is not relevant to the reaction, however, a preferable solvent is an alcohol such as methanol, ethanol etc., an ether such as tetrahydrofuran, dioxane etc., an ester such as ethyl acetate, methyl acetate etc., an aliphatic acid such as acetic acid, etc. and a mixture of an organic solvent mentioned above and water.

In the case that the protective group is aralkyl group, insoluble materials are filtered off from the reaction mixture after the reaction is completed, water and water-immiscible organic solvent are added to the filtrate in order to part the ingredients into aqueous and organic layers, and the aqueous layer is concentrated, whereby deprotected desired compound is obtained. This compound can further be purified, if necessary, by employing column chromatography, recrystallization, preparative thin layer chromatography etc.

In the case that allyl group is the protective group, after the reaction is completed, the reaction mixture is diluted with water and a water-immiscible solvent, and added with a weak alkali such as potassium hydrogen carbonate to make a weakly alkaline solution, and then the aqueous layer is separated and concentrated, whereby the desired compound can be obtained. The desired compound can further be purified by column chromatography, recrystallization or preparative thin layer chromatography, if necessary.

In the first to tenth processes among the processes mentioned above, there is described the general synthetic method of the present compounds. It is needless to say that the method can be employed quite similarly to the synthesis of optically active compounds.

When an optically active compound is employed as a comound of the general formula (7) or (8), even though the compound of the genral formula,

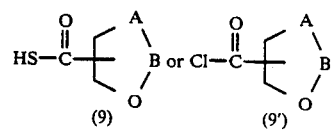

(wherein $-\left\langle\begin{array}{c}A\\B\\O\end{array}\right.$ denotes the same definition as above)

is a dl-compound, a single optically active compound is obtained, because optical resolution is carried out in one of the second, sixth or eighth process.

When the compound (7) or (8) is a dl-compound and the compound of the general formula,

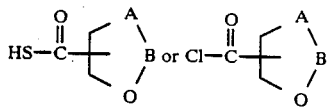

(wherein $-\left\langle\begin{array}{c}A\\B\\O\end{array}\right.$ denotes the same definition as above)

is an optically active single compound, optical resolution is carried out in a stage of the second, sixth or eighth process and an optically active single compound is obtained too.

As the means of the optical resolution, recrystallization, column chromatography or preparative thin layer chromatography is preferable.

A present compound of the general formula (1), wherein R is hydrogen, can be changed to a pharmacologically acceptable salt, if necessary. As the salt, there may be exemplified an inorganic salt such as lithium, sodium, potassium, calcium or magnesium salt, an amino acid salt such as lysine salt etc., or ammonium salt, and sodium or potassium salt is preferable.

Although the present penem compound represented by the general formula (1) exhisibits strong antibial activity in the form of a racemate, there may be exemplified as the most desirable form in the isomers, a compound which has (5R,6S) configuration and, with regard to 1-hydroxyethyl group of the substituent at 6-position, has R configuration.

The present compounds are novel compounds having strong antibial activity. It is clear from the comparison of antibial activity in vitro with other compounds which were synthesized separately by the present inventors. The compounds synthesized for this comparison include novel compounds as well as known compounds described in Jpanese Patent Application Disclosure Nos. 25110/1981 and 88291/1979.

The present compounds have antibial activity which is able to determine by standardized dilution assay method in vitro.

By employing such standardized microbiological method, it was found that the present compounds show activities in a test amount of 0.025 to 50 μg/mg against gram positive bacteria such as *Staphylococcus aureus*,

*Micrococcus luteus*, etc.; gram-negative bacteria such as *Escherichia coli, klebsiella pneumonia, Serratia marcescens, Proteus morganii, Enterobactor cloacae, Alkaliqenes faecalis* etc., *Proteus vulgaris;* anaerobic bacteria such as *Bacterioides fradillia* and *fusobacterium varium.*

The present compounds show not so high toxicity value ($LD_{50}$) in vivosimilarly to general penem compounds and can be prescribed for oral, parenteral and external administration.

Although the dose of the present compounds depends on many factors, a typical daily dose for an adult is 50 mg to 5 g and it is preferably administered at intervals in a daily amount of 100 mg to 4 g. In general, it may be administered with a dosage unit containing a suitable amount of the active ingredient and a biologically acceptable carrier or diluent.

For oral administration may be employed tablets or capsules which contain the active ingredient as well as a diluent, for example, lactose, glucose, sucrose, mannitol, sorbitol and cellulose, and a lubricant such as talc, stearic acid or its salt. The tablets may further contain a binder, for example, magnesium silicate, starch etc.

For parenteral administration, i.e. intramuscular and subsutaneous administration, it is suitable to employ an isotonic aqueous solution or an emulsion.

The present compounds may be employed not only for human use but for animal use too.

The protective group employed in the synthesis of the present compounds may be any protective group usually employed in the technical field of $\beta$-lactam compounds.

As a suitable protective group for hydroxyl group, there may be exemplified t-butylmethylsilyl group, t-butoxycarbonyl group, p-nitrobenzyloxycarbonyl group, 2,2,2-trichloroethoxycarbonyl group etc.

As a protective group for carboxylic group, there may be exemplified allyl group, 2,2,2-trichloroethyl group, t-butyl group, p-nitrobenzyl group etc., and allyl group is preferable.

In the following preparation examples, the active ingredient may be, for example, potassium (1'R,2"R,5R,6S)-6-(1'-hydroxyethyl)-2-(2"tetrahydrofuranyl)penem-3-carbonate or an equivalent amount of any other present compound.

PREPARATION EXAMPLE 1

| Capsules No. | Ingredients | mg/capsule | mg/capsule |
|---|---|---|---|
| 1 | Active ingredient | 250 | 100 |
| 2 | Corn starch | 20 | 10 |
| 3 | Magnesium stearate | 5 | 2 |
|  | Total amount | 275 | 112 |

(Preparation Procedure)

The ingredients of No. 1 and No. 2 were mixed in a suitable mixing machine, the ingredient No. 3 was added thereto and the mixture was further mixed. The mixed ingredients was filled into capsules employing a capsule-filling machine.

PREPARATION EXAMPLE 2

| Tablets No. | Ingredients | mg/tablet |
|---|---|---|
| 1 | Active ingredient | 250 |
| 2 | Lactose | 55 |
| 3 | Corn starch | 40 |
| 4 | Magnesium stearate | 5 |
|  | Total amount | 350 |

(Preparation Procedure)

The ingredients of No. 1 to No. 3 were mixed in a suitable mixing machine and then the ingredient No. 4 was added thereto and mixed for further several minutes. The mixture was compressed with a suitable tableting machine to a prescribed size and weight.

PREPARATION EXAMPLE 3

| Ampoules Ingredient | Amount (g) in a ampoule | | |
|---|---|---|---|
| Active ingredient | 1.0 g | 0.5 g | 0.25 g |

(Preparation Procedure)

A steriled aqueous solution of active ingredient was filled into an ampoule of 20 ml, 10 ml or 5 ml so as to make each ampoule contain 1.0 g, 0.5 g or 0.25 g of the active ingredient and sealed.

EXAMPLE 1

(1'R,2"R, 3S, 4R and 1'S,2"S, 3S, 4R and 1'S,2"R,3R,4S and 1'S, 2"S, 3R, 4S)-3-(1'-tert-butyldimethylsilyoxyethyl)-4-(2"-tetrahydrofuranoylthio)-2-azetidinone (2)

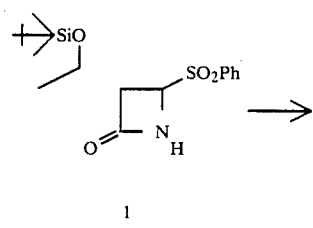

1

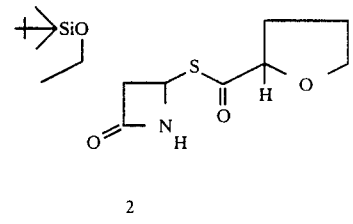

2

In acetone (40 ml) was dissolved (1'R, 3S, 4R and 1'S, 3R, 4S)-3-(1-tert-butyldimethylsilyloxyethyl)-4-phenylsulfonyl-2-azetidinone (1) (1.953 g, 5.29 mmole), and water (14 ml) was added to the solution. Tetrahydrofuran-2-thiocarboxylic acid (1.28 g, 9.68 mmole) was added to the resulting mixture, and 1N NaOH was added dropwise to the reaction mixture at 0° C. under stirring to adjust it to pH 11.0. Then, the mixture was adjusted to pH 7.0 with 1N HCl, and extracted with chloroform, and the organic layer was washed with water and dried with anhydrous sodium sulfate. The solvent was distilled off under reduced pressure, and the residue was purified by silica gel chromatography (70 g of silica gel, hexane:ethyl acetate=5:1) to give 1.139 g (60%) of the subject compound (2) in the form of a colorless oily material.

IR$_{max}^{film}$ (cm$^{-1}$): 3270(amide NH), 1782(lactam C=O), 1702 (thioester C=O).

NMR δ(CDCl$_3$): 1.20(1.5H,d,2'-position-CH$_3$), 1.21(1.5H,d, 2'-position-CH$_3$), 1.87–2.36(4H,m), 3.14–3.24 (1H,m,6-position-H), 3.92–4.20(2H,m), 4.20–4.33(1H,m,1'-position-H), 4.48(1H,dd,J=5 Hz, 15 Hz, 2''-position-H), 5.19(0.5H,d,J=2.3 Hz, 5-position-H), 5.23(0.5H,d,J=2.6 Hz,5-position-H), 6.28(0.5H,br.s,NH), 0.30(0.5H,br.s,NH).

EXAMPLE 2

(1'R,2''R, 3S,4R and 1'R, 2''S, 3S, 4R)-3-(1'-tert-butyl-dimethylsilyloxyethyl)-4-(2''-tetrahydrofuranoylthio)-2-azetidinone (4).

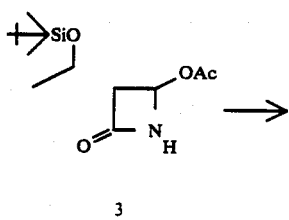

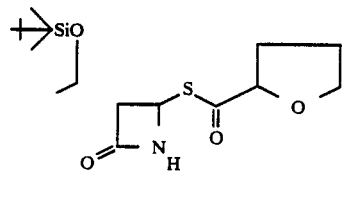

Tetrahydrofuran-2-thiocarboxylic acid (2.09 g, 15.8 mmole; 2R/2S=1/1 mixture) was added to a solution of (1'R, 3S, 4R)-4-acetoxy-3-(1'-tert-butyldimethylsilyloxyethyl)-2-azetidinone (3) (2.26 g, 7.9 mmole) in a mixture of tetrahydrofuran (170 ml) and water (60 ml). 1N sodium hydroxide was added dropwise to the mixture under stirring to adjust it to pH 7.3. Stirring was continued for 15 minutes, and further tetrahydrofuran-2-thiocarboxylic acdi (0.32 g, 2.4 mmole) was added to the mixture, followed by adjustment to pH 8.0 with 1N sodium hydroxide.

Water (50 ml) was added to the mixture, and the resulting mixture was extracted three times with ethyl acetate (150 ml). The organic layer was washed with water and dried with anhydrous sodium sulfate. The solvent was distilled off, and the resulting crude product was purified by silica gel chromatography to give 2.34 g (82%) of the subject compound (4) in the form of a colorless oily material.

EXAMPLE 3

(1'R, 2''S, 3S, 4R)-3-(1'-tert-butyldimethylsilyloxyethyl)-4-(2'-tetrahydrofuranoylthio)-2-azetidinone (5) and (1'R, 2''R, 3S, 4R)-3-(1'-tert-butyldimethylsilyloxyethyl)-4-(2''-tetrahydrofuranoyl)-2-azetidinone (6).

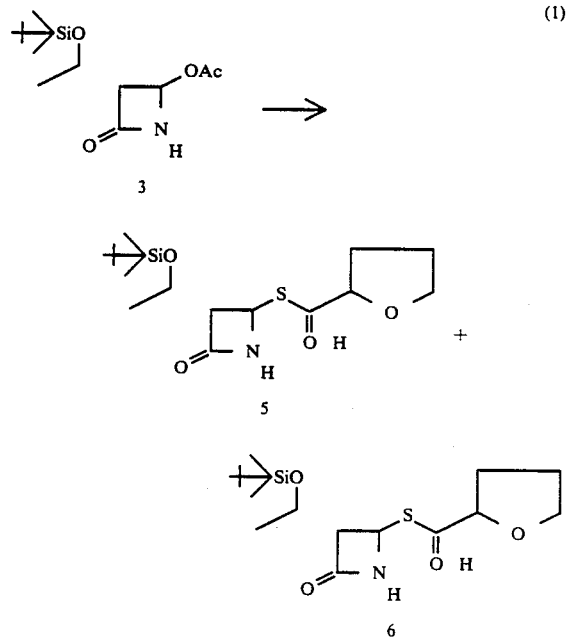

Tetrahydrofuran-2-thiocarboxylic acid (1.51 g, 14.7 mmole; 2R/2S=3/1 mixture as obtained by resolution) was added to a solution of (1'R, 3S, 4R)-4-acetoxy-3-(1'-tert-butyldimethylsolyloxyethyl)-2-azetidinone (3) (3.28 g, 11.4 mmole) in a mixture of tetrahydrofuran (170 ml) and water (60 ml), and the mixture was treated by the same procedure as described in Example 2. The resulting crude product was subjected to careful separation by means of flush chromatography (600 g of silica gel; 4% ethyl acetate-chloroform), and the first fraction was concentrated to give 1.09 g of (1'R, 2''S, 3S,4R)-3-(1'-tert-butyldimethylsilyloxyethyl)-4-(2'-tetrahydrofuranoylthio)-2-azetidinone (5) in the form of a colorless solid material.

IR$_{max}^{film}$ (cm$_{-1}$): 3310(NH), 1770(lactam C=O), 1688(thioester C=O).

NMR δ(CDCl$_3$): 0.08(6H,S), 0.88(9H,S), 1.19(3H,d,J=6.0 Hz, —CH—CH$_3$), 1.86–2.37(4H,m-CH$_2$ 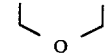 CH$_2$), 3.17 (1H,d,d,3-position-H), 3.91–4.12(2H,m, 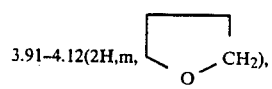 ), 4.21–4.32(1H,m,—CH—CH$_3$), 4.48(1H,d,d,J=5 Hz, 15 Hz, 2''-position-H), 5.23(1H,d,J=2.6 Hz, 4-position-H), 6.34(1H,br.S,NH).

The second fraction was concentrated to give 2.26 g of (1'R, 2''R, 3S, 4R)-3-(1'-tert-butyldimethylsilyloxyethyl)-4-(2''-tetrahydrofuranoylthio)-2-azetidinone (6) in the form of a colorless oily material. IR$_{max}^{film}$ (cm$^{-1}$): 3330(NH), 1778(lactam C=O), 1688(thioester C=O). NMR (CDCl$_3$): 0.08(6H,S), 0.88(9H,S), 1.21(3H,d,J=6 Hz, —CH—CH$_3$), 1.83–2.38 (4H,m, CH₂—CH₂ \ O /), 3.18 (1H,d,d, 3-position-H),

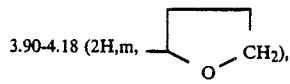
3.90–4.18 (2H,m, ), 4.20–4.33(1H,m,—CH—CH₃), 4.48(1H,d,d,J=5 Hz, 15 Hz, 2″-position-H), 5.19(1H,d,J=2.6 Hz,4-position-H), 6.40(1H,br.S,NH).

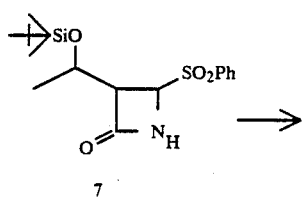

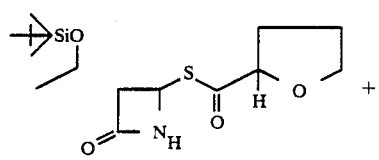

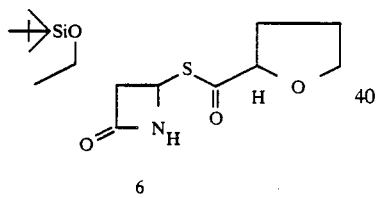

(1R, 3S, 4R)-3-(1′-tert-butyldimethylsilyloxyethyl)-4-phenylsulfonyl-2-azetidinone (7) (9.26 g, 25.06 mmole) and tetrahydrofuran-2-thiocarboxylic acid (4.96 g, 37.5 mmole; a 2R/2S=3/1 mixture as obtained by resolution) were treated by the same procedure as described in Example 1, and the resulting crude product was purified by flush chromatography (1200 g of silica gel, 4% ethyl acetate-chloroform) to give 1.67 g of (1′R, 2″S, 3S, 4R)-3-(1′-tert-butyldimethylsilyloxyethyl)-4-(2″-tetrahydrofuranoylthio)-2-azetidinone (5) in the form of a colorless solid material, whose spectrum data were found to be in complete accordance with those of the product as obtained in Example 3-(1). On the other hand, there was obtained 5.46 g of (1′R, 2″R, 3S, 4R)-3-(1′-tert-butyldimethylsilyloxyethyl)-4-(2″-tetrahydrofuranoylthio)-2-azetidinone (6) in the form of a colorless oily material, whose spectrum data were found to be in complete accordance with those of the product as obtained in Example 3-(2).

EXAMPLE 4

(1″R, 2″R, 3S, 4R and 1″R, 2″S, 3S, 4R and 1″S, 2″′R, 3R, 4S and 1″S, 2″′S,3R, 4S)-1-(1′-allyloxycarbonyl-2′-triphenylphosphoranilydenemethyl)-3-(1″-tert-butyldimethylsilyloxyethyl)-4-(2″-tetrahydrofuranoylthio)-2-azetidinone (10).

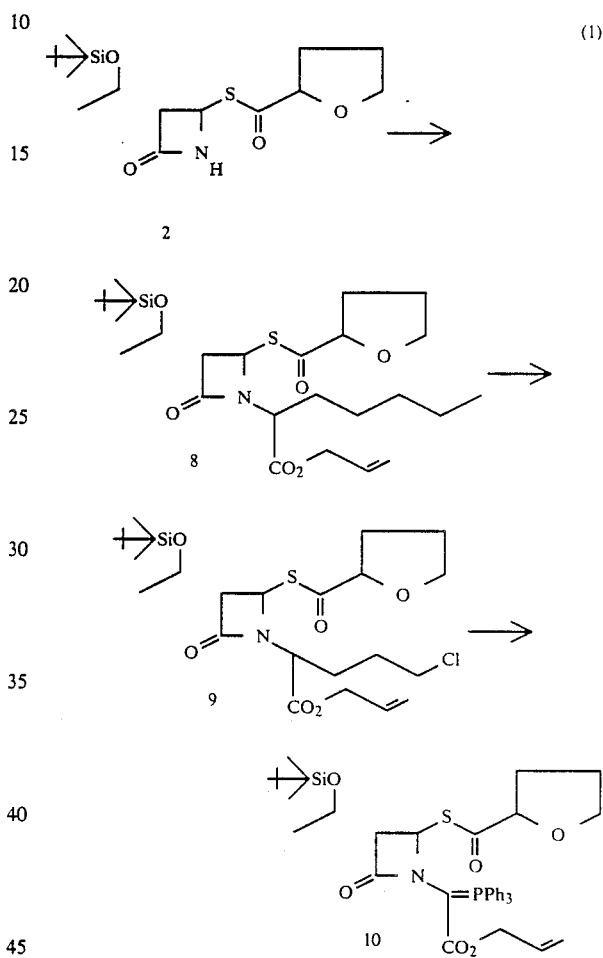

(1′R, 2″R, 3S, 4R and 1′R, 2″S, 3S, 4R and 1′S, 2″R, 3R, 4S and 1′S, 2″S, 3R, 4S)-3-(1′-tert-butyldimethylsilyloxyethyl)-4-(2″-tetrahydrofuranoylthio)-2-azetidinone (2) (1.225 g, 3.4 mmole) and allyl glyoxylate (0.540 g, 4.09 mmole) were dissolved in benzene (100 ml), and the solution was heated under reflux for 25 hours, where by the azeotropized water was removed through Molecular sieves 4A. The benzene was distilled off under reduced pressure, and the resulting alcohol compound (8) was used without being purified.

The crude alcohol compound (8) (1.61 g) was dissolved in tetrahydrofuran (5 ml), and 2,6-lutidine (0.48 ml) was added to the solution, followed by stirring at −10° C. Thionyl chloride (0.25 ml) was added to the mixture, which was then transferred into ice-cold water (50 ml) 20 minutes later, followed by extraction three times with chloroform. The chloroform layer was washed with water, dried over anhydrous sodium sulfate and freed of the solvent under reduced pressure. The resulting crude product was purified by flush chromatography (35 g of silica gel, ethyl acetate:hexane=1:3) to give 1.242 g (74%) of (1″R, 2″′R, 3S, 4R and 1″R, 2‴S, 3S, 4R and 1″S, 2‴R, 3R, 4S and 1″S, 2‴S, 3R, 4S)-1-(1′-allyloxycarbonyl-2′-chloromethyl)-3-(1″-tert-butylmethylsilyloxyethyl)-4-(2‴-tetrahydrofuranoylthio)-2-azetidinone (9) in the form of a yellowish oily material.

A mixture of the chlorinated compound (9) (1.242 g, 2.52 mmole), triphenylphosphine (1.322 g, 5.04 mmole) and 2,6-lutidine (0.324 g, 3.02 mmole) was dissolved in tetrahydrofuran (15 ml), and the solution was stirred at 55° to 60° C. for 75 hours. The insoluble matter was filtered out, and the filtrate was diluted with ethyl acetate, washed with water and dried over anhydrous sodium sulfate. The solvent was distilled off and the resulting crude product was purified by flush chromatography (80 g of silica gel, ethyl acetate:hexane=1:2) to give 0.854 g (47%) of the subject compound (10) in the form of a colorless oily material.

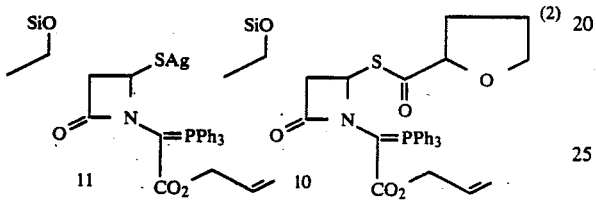

(1′R, 3S, 4R and 1″, 3R, 4S)-1-(1′-allyloxycarbonyl-2′-triphenylphophoranilydenemethyl)-3-(1″-tert-butyl-dimethylsilyloxyethyl)-4-silver-thio-2-azetidinone (11) (0.614 g) was dissolved in methylene chloride (5 ml), and a solution of 2-tetrahydrofurancarboxyl chloride (0.117 g) in methylene chloride (1 ml) was added to the solution at 0° C., followed by stirring at 0° C. for 15 minutes and at room temperature for 15 minutes. The insoluble matter was filtered out, and the filtrate was washed with saturated aqueous sodium hydrogen-carbonate and water, successively, and dried over anhydrous sodium sulfate. The solvent was distilled off, and the resulting crude product was purified by flush chromatography to give 0.295 g (71%) of the subject compound (10) in the form of a less oily material.

EXAMPLE 5

(1″R, 2‴R, 3S, 4R and 1″R, 2‴S, 3S, 4R)-1-(1′-allyloxycarbonyl-2′-triphenylphosphoranylydenemethyl)-3-(1″-tert-butyldimethylsilyloxyethyl)-4-(2‴-tetrahydrofuranoylthio)-2-azetidinone (14)

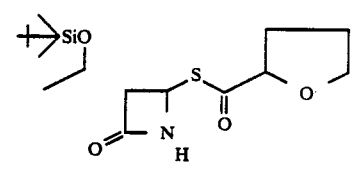

4

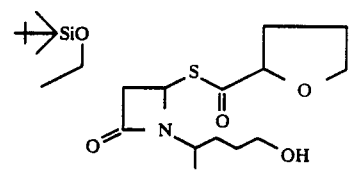

12

-continued

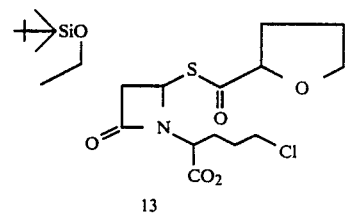

13

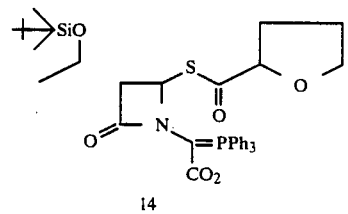

14

(1′R, 2″R, 3S, 4R and 1′R, 2″S, 3S, 4R)-3-(1′-tert-butyldimethylsilyloxyethyl)-4-(2′-tetrahydrofuranoylthio)-2-azetidinone (4) (2.44 g, 6.79 mmole) was treated by the same procedure as described in Example 3-(1) to give 1.21 g (30%) of the subject compound (14) in the form of a colorless amorphous material.

EXAMPLE 6

(1″R, 2‴S, 3S, 4R)-1-(1′-allyloxycarbonyl-2′-triphenylphosphoranylydenemethyl)-3-(1″-tert-butyldimethylsilyloxy)-4-(2‴-tetrahydrofuranoylthio)-2-azetidinone (17).

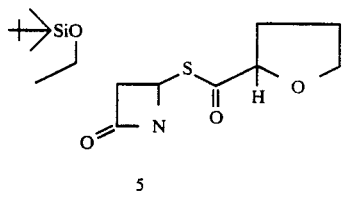

5

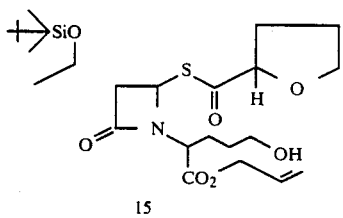

15

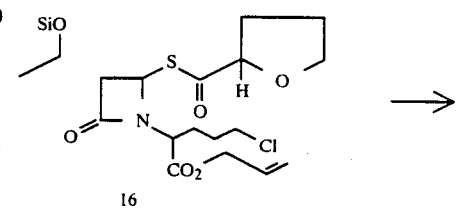

16

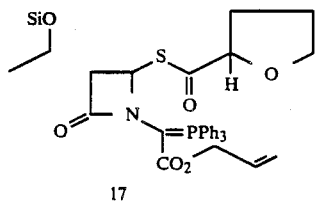

(1'R, 2"S, 3S, 4R)-3-(1'-tert-butyldimethylsilyloxyethyl)-4-(2"-tetrahydrofuranoylthio)-2-azetidinone (5) (1.09 g, 3.03 mmole) was treated by the same procedure as described in Example 3-(1) to give 0.39 g (18%) of the subject compound (17) in the form of a colorless amorphous material.

EXAMPLE 7

(1"R, 2'''R, 3S, 4R)-1-(1'-allyloxycarbonyl-2'-triphenylphosphalinilydenemethyl)-3-(1"-tert-butyldimethylsilyloxyethyl)-4-(2'''-tetrahydrofuranoylthio)-2-azetidinone (20)

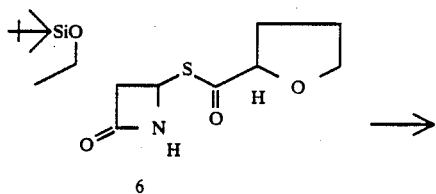

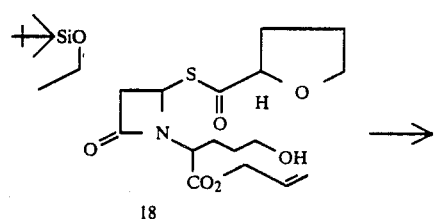

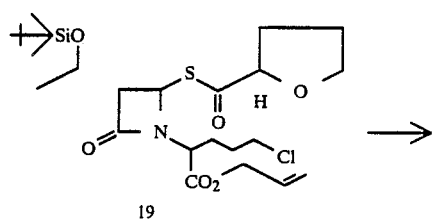

(1'R, 2"R, 3S, 4R)-3-(1'-tert-butyldimethylsilyloxyethyl)-4-(2"-tetrahydrofuranoylthio)-2-azetidinone (6) (4.96 g, 13.79 mmole) was treated by the same procedure as described in Example 3-(1) to give 1.62 g(36%) of the subject compound in the form of a colorless amorphous material.

EXAMPLE 8

(1"R, 3'''R, 3S, 4R and 1"R, 3'''S, 3S, 4R)-1-(1'-allyloxycarbonyl-2'-triphenylphosphranilydenemethyl)-3-(1"-tert-butyldimethylsilyloxyethyl)-4-(3'''-tetrahydrofuranoylthio)-2-azetidinone (22).

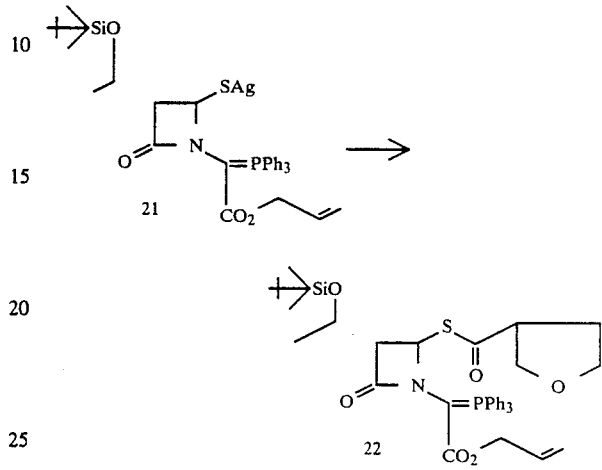

(1"R, 3S, 4R)-1-(1'-allyloxycarbonyl-2'-triphenylphosphranilydenemethyl)-3-(1"-tert-butyldimethylsilyloxyethyl)-4-silverthio-2-azetidinone (2) (1.88 g) and 3-tetrahydrofurancarboxyl chloride (0.404 g) were treated by the same procedure as described in Example 3-(2) to give 1.048 g (73%) of the subject compound (22) in the form of a colorless amorphous material.

EXAMPLE 9

(1"R, 2'''R, 3S, 4R and 1"R, 2'''S, 3S, 4R)-1-(1'-allyloxycarbonyl-2'-triphenylphosphoranilydenemethyl)-3-(1"-tert-butyldimethylsilyloxyethyl)-4-(2'''-tetrahydropyranoylthio)-2-azetidinone (23).

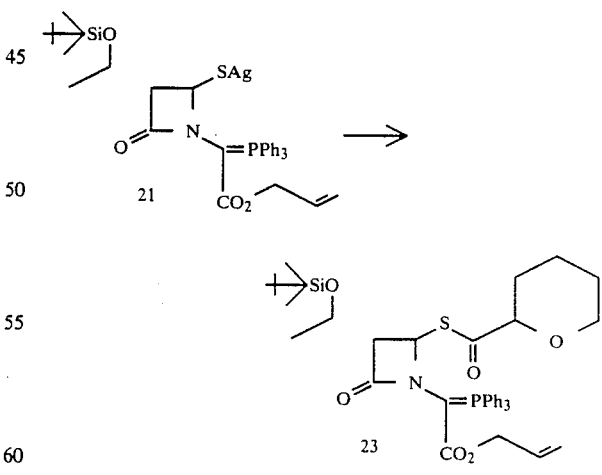

(1"R, 3S, 4R)-1-(1'-allyloxycarbonyl-2'-triphenylphosphoranilydenemethyl)-3-(1"-tert-butyldimethylsilyloxyethyl)-4-Silverthio-2-azetidinone (21) (1.88 g) and 2-tetrahydropyranecarboxyl chloride (0.385 g) were treated by the same procedure as described in Example 3-(2) to give 1.033 g of the subject compound (23) in the form of a yellowish amorphous material.

EXAMPLE 10

(1"R, 2'''R, 3S, 4R and 1"R, 2'''S, 3S, 4R)-1-(1'-allyloxycarbonyl-2-triphenylphosphranilydenemethyl)-3-(1"-tert-butyldimethylsilyloxyethyl)-4-(2"'-para-dioxanoylthio)-2-azetidinone (24).

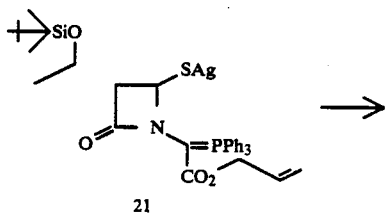

21

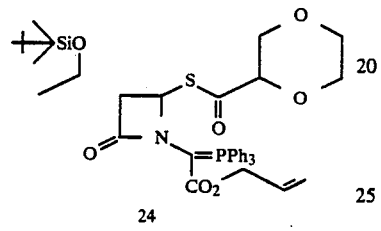

24

(1"R, 3S, 4R)-1-(1'-allyloxycarbonyl-2'-triphenylphosphranilidenemethyl)-3-(1"-tert-butyldimethylsilyloxyethyl)-4-silverthio-2-azetidinone (21) (1.88 g) and 2-para-dioxanecarboxyl chloride (0.389 g) were treated by the same procedure as described in Example 3-(2) to give 1.007 g (68.6%) of the subject compound (24) in the form of a yellowish oily material.

EXAMPLE 11

(1"R, 2'''S, 3S, 4R and 1"S, 2'''S, 3R, 4S)-1-(1'-allyloxycarbonyl-2'-triphenylphosphoranilidenemethyl)-3-(1'-tert-butyldimethylsilyloxyethyl)-4-[2'''-(5'''-oxo)oxolanoylthio]-2-azetidinone (25).

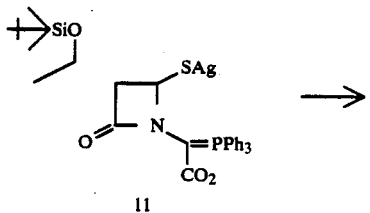

11

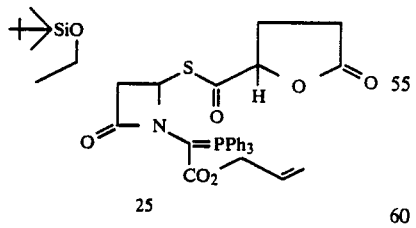

25

(1"R, 3S, 4R and 1"S, 3R, 4S)-1-(1'-allyloxycarbonyl-2'-triphenylphosphoranilidenemethyl)-3-(1"-tert-butyldimethylsilyloxyethyl)-4-silverthio-2-azetidinone (11) (0.363 g) and (2S)-2-(5-oxo)oxolanylcarboxyl chloride were treated by the same procedure as described in Example 3-(2) to give 0.25 g of the subject compound (25).

EXAMPLE 12

(1"R, 2'''R, 3S, 4R and 1"S, 2'''R, 3R, 4S)-1-(1'-allyloxycarbonyl-2'-triphenylphosphranilidenemethyl)-3-(1"-tert-butyldimethylsilyloxyethyl)-4-[2"'-(5'''-oxo)oxolanoylthio]-2-azetidinone (26).

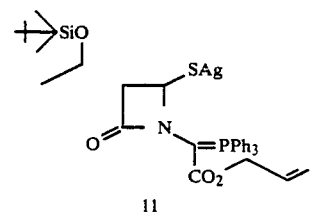

11

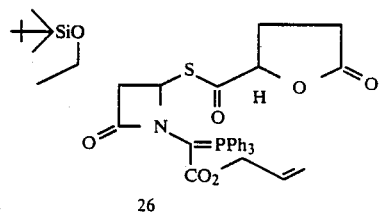

26

(1"R, 3S, 4R and 1"S, 3R, 4S)-1-(1'-allyloxycarbonyl-2'-triphenylphosphoranilidenemethyl)-3-(1"-tert-butyldimethylsilyloxyethyl)-4-silverthio-2-azetidinone (11) (0.363 g) and (2R)-2-(5-oxo)oxolanylcarboxyl chloride were treated by the same procedure as described in Example 3-(2) to give 0.162 g of the subject compound (26).

EXAMPLE 13

(1"R, 2'''R, 3S, 4R and 1", 2'''S, 3S, 4R and 1"S, 2'''R, 3R, 4S and 1"S, 2'''S, 3R, 4S)-1-(1'-allyloxycarbonyl-2'-triphenylphosphoranilidenemethyl)-3-(1"-hydroxyethyl)-4-(2'''-tetrahydrofuranoylthio)-2-azetidinone (27).

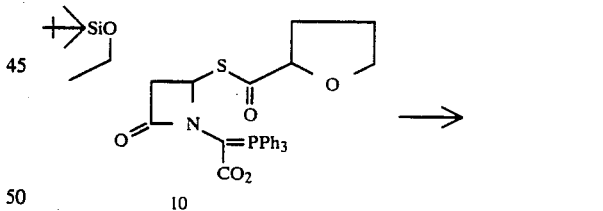

10

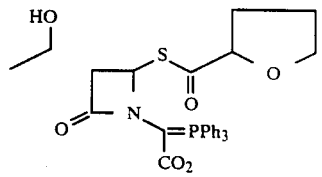

27

In tetrahydrofuran (2 ml) was dissolved (1"R, 2'''R, 3S, 4R and 1"R, 2'''S, 3S, 4R and 1"S, 2'''R, 3R, 4S and 1"S, 2'''S, 3R, 4S)-1-(1'-allyloxycarbonyl-2'-triphenylphosphoranilidenemethyl)-3-(1"-tert-butyldimethylsilyloxyethyl)-4-(2'''-tetrahydrofuranoylthio)-2-azetidinone (10) (0.295 g, 0.41 mmole), and a mixture of acetic acid (206 μl) and tetrahydrofuran (1 ml) was added to the solution. Then, tetra-n-butylammonium bromide (a 1M solution in tetrahydrofuran, 1.23 ml) was added to the mixture, followed by stirring at room temperature for 62 hours. The reaction solution was diluted with ethyl acetate, washed with saturated sodium hydrogencarbonate solution and water, successively, and dried over anhydrous sodium sulfate. The solvent was distilled off, and the resulting crude product was purified by flush chromatography (10 g of silica gel, ethyl acetate:hexane=1:2) to give 0.12 g (48%) of the subject compound.

EXAMPLE 14

(1″R, 2‴R, 3S, 4R)-1-(1′-allyloxycarbonyl-2′-triphenylphosphoranilidenemethyl)-3-(1″-hydroxyethyl)-4-(2‴-tetrahydrofuranoylthio)-2-azetidinone (28).

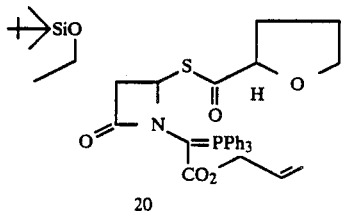

20

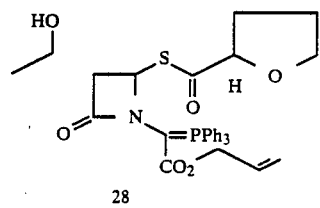

28

(1′R, 2″S, 3S, 4R)-1-(1′-allyloxycarbonyl-2′-triphenylphosphoranilidenemethyl)-3-(1″-tert-butyldimethylsilyloxyethyl)-4-(2″-tetrahydrofuranoylthio)-2-azetidinone (20) (1.40 g, 1.95 mmole) and acetic acid (0.98 ml) as well as tetra-n-butylammonium fluoride (a 1M solution in tetrahydrofuran, were subjected to the same procedure as described in Example 13 to give 1.03 g (87%) of the subject compound.

EXAMPLE 15

(1″R 2‴S, 3R, 4S and 1″S, 2‴S, 3S, 4R)-1-(1′-allyloxycarbonyl-2′-triphenylphosphoranilidenemethyl)-3-(1″-hydroxyethyl)-4-[2‴-(5‴-oxo)oxolanoylthio]-2-azetidinone (29).

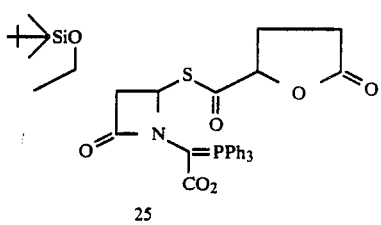

25

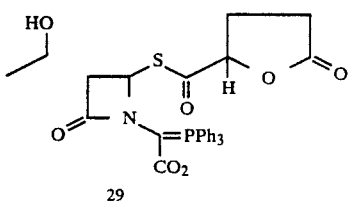

29

(1″R, 2‴R, 3S, 4R and 1″S, 2‴R, 3R, 4S)-1-(1′-allyloxycarbonyl-2′-triphenylphosphoranilidenemethyl)-3-(1″-tert-butyldimethylsilyloxyethyl)-4-[2‴-(5‴-oxo) oxolanoylthio]-2-azetidinone (25) (0.25 g, 0.34 mmole), acetic acid (0.2 ml) and tetra-n-butylammonium fluoride (a 1M solution in tetrahydrofuran, 0.9 ml) were subjected to the same procedure as described in Example 13 to give 0.060 g of the subject compound.

EXAMPLE 16

Allyl (1′R, 2″S, 5R, 6S)-6-(1′-tert-butyldimethylsilyloxyethyl)-2-(2″-tetrahydrofuranyl)penem-3-carboxylate (30) and allyl (1′R, 2″R, 5R, 6S)-6-(1′-tert-butyldimethylsilyloxyethyl)-2-(2″-tetrahydrofuranyl)-penem-3-carboxylate (31)

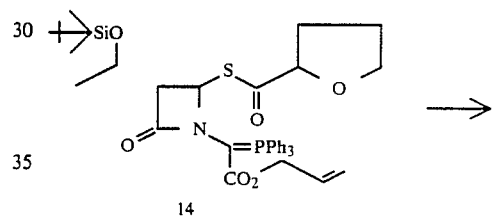

14

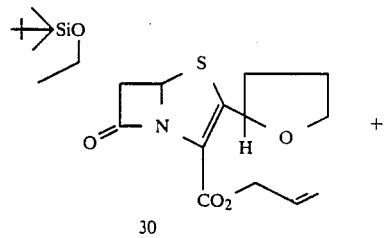

30

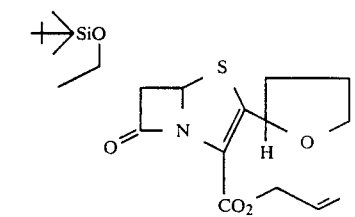

31

A mixture of (1″R, 2‴R, 3S, 4R and 1″R, 2‴S, 3S, 4R)-1-(1′-allyloxycarbonyl-2′-triphenylphosphoranilidenemethyl)-3-(1″-tert-butyldimethylsilyloxyethyl)-4-(2‴-tetrahydrofuranoylthio)-2-azetidinone (14) (1.21 g, 1.69 mmole) and toluene (120 ml) was refluxed for 16 hours, and cooled, followed by distilling off the solvent. The resulting crude product was purified carefully by flush chromatography (90 g of silica gel, ethyl acetate:hexane=1:15) to give 0.247 g (33%) of allyl (1′R, 2″S, 5R, 6S)-6-(1′-tert-butyldimethylsiloxyethyl)-2-(2″-tetrahydrofuranyl)penem-3-carboxylate (30), along with 0.312 g (42%) of allyl (1′R, 2″R, 5R, 6S)-6-(1′-tert-butyldimethylsilyloxyethyl)-2-(2″-tetrahydrofuranyl)penem-3-carboxylate (31).

EXAMPLE 17

Allyl (1′R, 2″S, 5R, 6S)-6-(1′-tert-butyldimethylsilyloxyethyl)-2-(2″-tetrahydrofuranyl)penem-3-carboxylate (30).

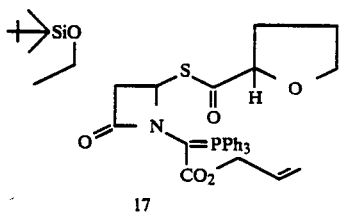

17

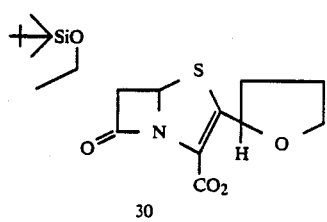

30

A mixture of (1″R, 2S′″S, 3S, 4R)-1-(1′-allyloxycarbonyl-2′-triphenylphosphoranilidenemethyl)-3-(1″-tert-butyldimethylsilyloxyethyl)-4-(2″′-tetrahydrofuranoylthio)-2-azetidinone (17) (0.394 g, 0.55 mmole) and toluene (40 ml) was subjected to the same procedure as described in Example 16 to give 0.176 g (73%) of the subject compound.

EXAMPLE 18

Allyl (1′R, 2″R, 5R, 6S)-6-(1′-tert-butyldimethylsilyloxyethyl)-2-(2″-tetrahydrofuranyl)penem-3-carboxylate (31).

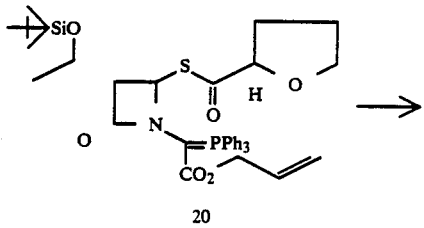

20

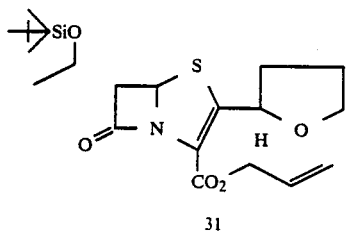

31

A mixture of (1″R, 2′″R, 3S, 4R)-1-(1′-allyloxycarbonyl-2′-tripehnylphosphoranilidenemethyl)-3-(1″-tert-butyldimethylsilyloxyethyl)-4-(2″′-tetrahydrofuranoylthio)-2-azetidinone (20) (2.04 g, 2.84 mmole) and toluene (200 ml) was subjected to the same procedure as described in Example 16 to give 1.12 g (89.8%) of the subject compound.

EXAMPLE 19

Allyl (1′R, 3″S, 5R, 6S)-6-(1′-tert-butyldimethylsilyloxyethyl)-2-(3″-tetrahydrofuranyl)penem-3-carboxylate (32) and allyl (1′R, 3″R, 5R, 6S)-6-(1′-tert-butyldimethylsilyloxyethyl)-2-(3″-tetrahydrofuranyl)penem-3-carboxylate (33).

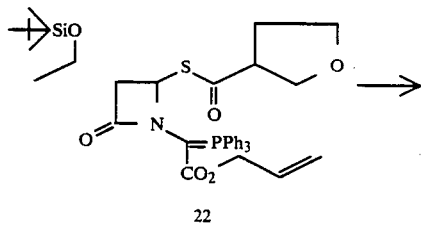

22

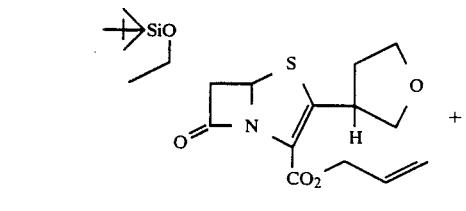

32

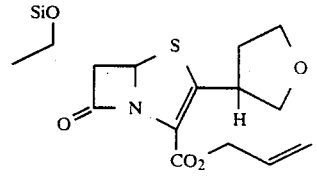

33

A mixture of (1″R, 3′″R, 3S, 4R and 1″R, 3′″S, 3S, 4R)-1-(1′-allyloxycarbonyl-2′-triphenylphosphoranilydenemethyl)-3-(1″-tert-butyldimethylsilyloxyethyl)-4-(3″′-tetrahydrofuranoylthio)-2-azetidinone (22) (1.048 g, 1.46 mmole) and toluene (100 ml) was subjected to the same procedure as described in Example 16 to give 0.32 g (50%) of the subject compound (32) and 0.286 g (46%) of the subject compound (33).

EXAMPLE 20

Allyl (1′R, 2″S, 5R, 6S)-6-(1′-tert-butyldimethylsilyloxyethyl)-2-(2″-tetrahydropyranyl)penem-3-carboxylate (34) and allyl (1′R, 2″R, 5R, 6S)-6-(1′-tert-butyldimethylsilyloxyethyl)-2-(2″-tetrahydropyranyl)penem-3-carboxyalte (35).

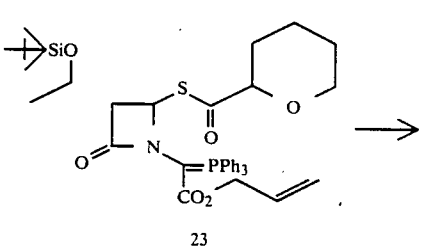

23

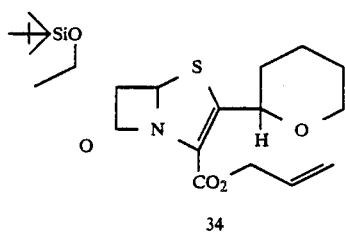

34

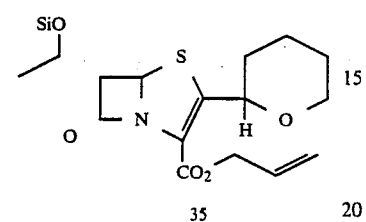

35

A mixture of (1″R, 2‴R, 3S, 4R and 1″R, 2‴S, 3S, 4R)-1-(1′-allyloxycarbonyl-2′-triphenylphosphoranilydenemethyl)-4-(2″-tetrahydropyranoylthio)-3-(1″-tert-butyldimethylsilyloxyethyl)-2-azetidinone (23) (1.033 g, 1.41 mmole) and toluene was subjected to the same procedure as described in Example 16 to give 0.194 g (30.3%) of the subject compound (34) and 0.189 g (29.5%) of the subject compound (35).

EXAMPLE 21

Allyl (1′R, 2″S, 5R, 6S and 1′R, 2″R, 5R, 6S)-6-(1′-tert-butyldimethylsilyloxyethyl)-2-(2″-para-dioxanyl)penem-3-carboxylate (36).

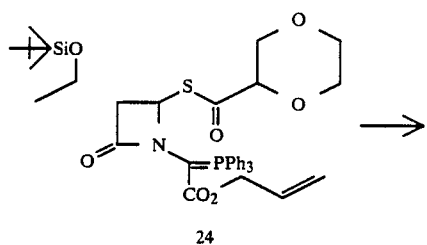

24

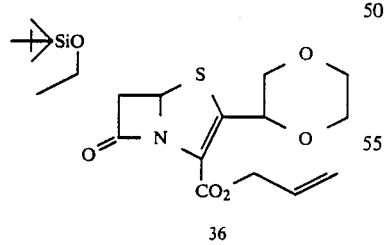

36

A mixture of (1″R, 2‴R, 3S, 4R and 1″R, 2‴S, 3S, 4R)-1-(1′-allyloxycarbonyl-2′-triphenylphosphranilydenemethyl)-4-(2″-para-dioxanoylthio)-3-(1″-tert-butyldimethylsilyloxyethyl)-2-azetidinone (24) (1.007 g, 1.37 mmole) and toluene (70 ml) was subjected to the same procedure as described in Example 16 to give 0.496 g (79.5%) of the subject compound.

EXAMPLE 22

Allyl (1′R, 2″S, 5R, 6S)-6-(1′-tert-butyldimethylsilyloxyethyl)-2-(2″-para-dioxanyl)penem-3-carboxyalte (37) and all (1′R, 2″R, 5R, 6S)-6-(1′-tert-butyldimethylsilyloxyethyl)-2-(2″-para-dioxanyl)penem-3-carboxylate (38).

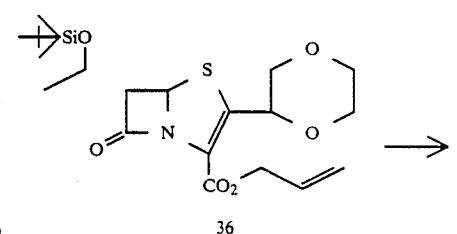

36

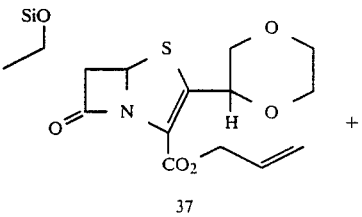

37

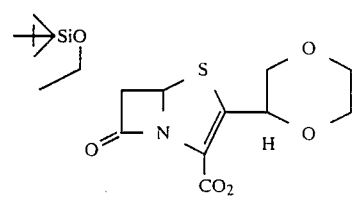

38

The isomer mixture as obtained in Example 21, allyl (1′R, 2″S, 5R, 6S and 1′R, 2″R, 5R, 6S)-6-(1′-tert-butyldimethylsilyloxyethyl)-2-(2″-para-dioxanyl)penem-3-carboxylate (36), (0.333 g) was subjected to separation by use of PLC 13895 (developed five times with chloroform) to give 0.1647 g (49.5%) of the subject compound (37) and 0.1544 g (46.4%) of the subject compound (38).

EXAMPLE 23

Allyl (1′R, 2″R, 5R, 6S)-6-(1′-tert-butyldimethylsilyloxyethyl)-2-[2″-(5″-oxo)oxolanyl]penem-3-carboxylate (39) and allyl (1′S, 2″R, 5S, 6R)-6-(1′-tert-butyldimethylsilyloxyethyl)-2-[2″-(5″-oxo)oxolanyl]penem-3-carboxylate (40).

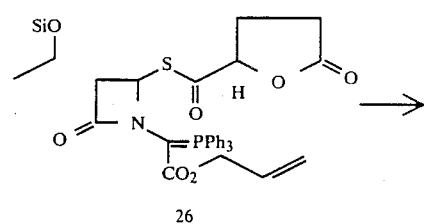

26

-continued

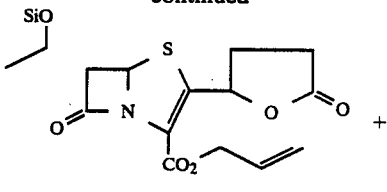

39

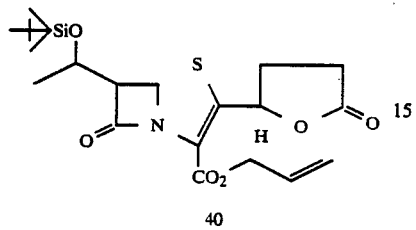

40

A mixture of (1"R, 2'"R, 3S, 4R and 1", 2'"R, 3R, 4S)-1-(1'-allyloxycarbonyl-2'-triphenylphosphoranilydenemethyl)-3-(1"-tert-butyldimethylsilyloxyethyl)-4-[2'"-(5'"-oxo)oxolanoylthio]-2-azetidinone (26) (0.162 g, 0.22 mmole) and toluene (50 ml) was subjected to the same procedure as described in Example 16 to give 23 mg (23%) of the subject compound (39) and 30 mg (30%) of the subject compound (40).

| Example No. | Comp'd. No. | Reaction time, hr. | % | $IR^{film}_{max}$ (cm$^{-1}$) C=O | Ester C=O |
|---|---|---|---|---|---|
| 16 | 30 | 16 | 33 | 1770 | 1705 |
|  | 31 |  | 42 | 1770 | 1695 |
| 17 | 30 | 16 | 73 |  |  |
| 18 | 31 | 5 | 90 |  |  |
| 19 | 32 | 24 | 51 | 1770 | 1704 |
|  | 33 |  | 46 | 1770 | 1700 |
| 20 | 34 | 18 | 30 | 1782 | 1703 |
|  | 35 |  | 30 | 1795 | 1708 |
| 21 | 36 | 10 | 80 |  |  |
| 22 | 37 | 16 | 49 | 1786 | 1718 |
|  | 38 |  | 47 | 1790 | 1708 |
| 23 | 39 | 0.2 | 30 |  |  |
|  | 40 |  | 23 |  |  |

| Comp'd. No. | NMR Spectrum Data δ (CDCl$_3$) |
|---|---|
| 30 | 0.07(6H,S), 0.88(9H,S), 1.25(3H,d,J=6Hz,2"-position-CH$_3$), 1.67-2.06(3H,m), 2.34-2.49(1H,m), 3.66(1H,d,d,J=5Hz,6-position-H), 3.75-4.00(2H,m), 4.14-4.26(2H,m,1'-position-H), 4.58-4.76(2H,m), 5.23-5.44(2H,m, —CH=CH$_2$), 5.54(1H,d,J=1.7Hz,5-position-H), 5.83-5.99(1H,m,—CH=CH$_2$) |
| 31 | 0.08(6H,S), 0.88(9H,S), 1.24(3H,d,J=6Hz,2"-position-CH$_3$), 1.74-2.10(3H,m), 2.38-2.53(1H,m), 3.67(1H,d,d,J=5Hz, 6-position-H), 3.78-4.04(2H,m), 4.16-4.30(1H,m,1'-position-H), 4.58-4.76(2H,m,O—CH$_2$—CH), 5.24-5.43(2H,m, —CH=CH$_2$), 5.47(1H,d,J=2Hz,5-position-H), 5.84-6.02(1H,m,—CH=CH$_2$) |
| 32 | 0.08(6H,S), 0.88(9H,S), 1.25(3H,d,J=6.6Hz,2'-position-CH$_3$), 1.78-1.94(1H,m), 2.17-2.33(1H,m), 3.66(1H,d,d,J=1.3Hz,4.6Hz,6-position-H), 3.63-3.85(2H,m), 3.90-4.05(2H,m), 4.19-4.30(1H,m,1'-position-H), 4.37-4.52(1H,m), 4.60-4.80(2H,m,O—CH$_2$—CH=), 5.24(1H,d,d,J=1.3Hz,10.6Hz, —CH=CH$_2$), 5.40(1H,d,d,J=1.3Hz,7.2Hz,—CH=CH$_2$), 5.52(1H, d,J=2.0Hz,5-position-H), 5.86-6.02(1H,m,—CH=CH$_2$) |
| 33 | 0.08(6H,S), 0.88(9H,S), 1.24(3H,d,J=5.9Hz,2'-position-CH$_3$), 1.87-2.04(2H,m), 3.60-3.76(2H,m), 3.89-4.05(2H,m), 3.76-3.89(1H,m), 4.18-4.32(1H,m,1'-position-H), 4.38-4.53(1H,m), 4.60-4.80(2H,m,—O—CH$_2$—CH=), 5.24 |

-continued

| Comp'd. No. | NMR Spectrum Data δ (CDCl$_3$) |
|---|---|
|  | (1H,d,d, J=1.4Hz,10.6Hz,—CH=CH$_2$), 5.24(1h,d,d, J=1.3Hz,16.5Hz —CH=CH$_2$), 5.55(1H,d,J=1.3Hz,5-position-H), 5.85-6.03 (1H,m,—CH=CH$_2$) |
| 34 | 0.06(6H,S), 0.88(9H,S), 1.24(3H,d,J=6.00Hz,2"-position-CH$_3$), 1.47-1.95(6H,m), 3.46-3.57(1H,br.t), 3.66(1H,d,d, J=1.35Hz,4.86Hz,6-position-H), 3.96-4.04(1H,br.d), 4.21(1H,d,q,J=4.86Hz,6.00Hz,1'-position-H), 4.58-4.76 (2H,m,—O—CH$_2$—CH=), 4.99-5.05(1H,m), 5.21-5.47 (2H,m,CH=CH$_2$), 5.51(1H,d,J=1.35Hz,5-position-H), 5.85-6.01(1H, m,—CH=CH$_2$) |
| 35 | 0.06(6H,S), 0.86(9H,S), 1.24(3H,d,J=5.94Hz,2"-position-CH$_3$), 1.45-1.96(6H,m), 3.66(1H,d,d,J=1.30Hz,5.94Hz,6-position-HO, 3.50-4.05(2H,m), 4.20(1H,d,q,J=5.94Hz, 5.94Hz,1'-position-H), 4.61-4.76(2H,m, —O—CH$_2$—CH=), 5.04-5.08(1H,m), 5.22-5.43(2H,m, CH=CH$_2$), 5.55(1H,d,J=1.3-Hz, 5-position-H), 5.85-6.00(1H,m,—CH=CH$_2$) |
| 37 | 0.07(6H,S), 0.88(9H,S), 1.24(3H,d,J=5.94Hz,2'-position-CH$_3$), 3.33-3.95(7H,m), 4.21(1H,d,q,J=5.94Hz,5.44Hz, 1'-position-H), 4.62-4.78(2H,m O—CH$_2$—CH=), 5.23-5.48 (3H,m), 5.56(1H,d,J=1.32Hz,5-position-H), 5.85-6.00 (1H,m,—CH=CH$_2$) |
| 38 | 0.07(6H,S), 0.88(9H,S), 1.24(3H,d,J=6.60Hz,2'-position-CH$_3$), 3.41-3.97(7H,m), 4.22(1H,d,q,J=5.93Hz), 4.62-4.76 (2H,m,—O—CH$_2$—CH=), 5.22-5.48(3H,m), 5.51(1H, d,J=1.32Hz, 5-position-H), 5.85-6.02(1H,m, —CH=CH$_2$) |
| 39 | 0.06(6H,S), 0.87(9H,S), 1.23(3H,d,J=6Hz,2'-position-CH$_3$), 2.10-2.20 and 2.50-2.80(4H,m), 3.74(1H,d,d,J=2Hz, 6-position-H), 4.2-4.3(1H,m,1'-position-H), 4.6-4.8 (2H,m,—O—CH$_2$—CH=), 5.25(1H,d,J=1Hz,10Hz, CH=CH$_2$), 5.40 (1H,d,J=17Hz,—CH=CH$_2$), 5.59(1H, d,J=2Hz,5-position-H), 5.92-5.99(1H,m,CH=CH$_2$), 6.02(1H,t,J=7Hz,2"-position-H) |
| 40 | 0.07(6H,S), 0.87(9H,S), 1.23(3H,d,J=6Hz,2'-position-CH$_3$), 2.05-2.2 and 2.6-2.8(4H,m), 3.72(1H,d,d,J=2Hz, 4Hz,6-position-H), 4.23(1H,m,1'-position=H), 4.6-4.8 (2H,m,—O—CH$_2$—CH$_2$=), 5.25(1H,d,d,J=1Hz,10Hz, —CH=CH$_2$), 5.39(1H,d,d,J=1Hz,17Hz,—CH=CH$_2$), 5.65(1H,d,J=2Hz,5-position-H), 5.85-6.0(1H,m, —CH=CH$_2$), 6.10(1H,t,J=7Hz, 2"-position-H). |

EXAMPLE 24

Allyl (1'R, 2"S, 5R, 6S)-6-(1'-hydroxyethyl)-2-(2"-tetrahydrofuranyl)-penem-3-carboxylate (41)

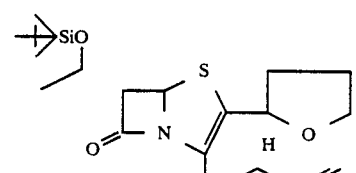

30

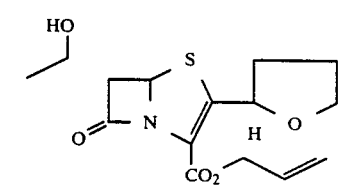

41

Allyl (1"R, 2"S, 5R, 6S)-6-(1'-tert-butyldimethylsilyloxyethyl)-2-(2"-tetrahydrofuranyl)penem-8-carboxylate (30) (0.176 g, 0.40 mmole), acetic acid (201 μl) and tetra-n-butylammonium fluoride (1.2 ml of a 1M solution in tetrahydrofuran) were subjected to the same procedure as described in Example 15 to give 0.105 g (86%) of the subject compound (41).

EXAMPLE 25

Allyl (1'R, 2"R, 5R, 6S)-6-(1'-hydroxyethyl)-2-(2"-tetrahydrofuranyl)-penem-3-carboxylate (42)

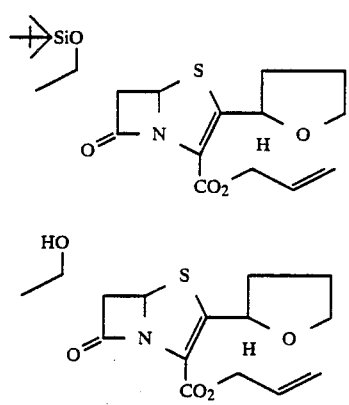

Allyl (1'R, 2"R, 5R, 6S)-6-(1'-tert-butyldimethylsilyloxyethyl)-2-(2"-tetrahydrofuranyl)penem-3-carboxylate (31) (1.12 g, 2.55 mmole), acetic acid (1.28 ml) and tetra-n-butylammonium fluoride (7.64 ml of a 1M solution in tetrahydrofuran) were subjected to the same procedure as described in Example 15 to give 0.877 g of the subject compound (42).

EXAMPLE 26

Allyl (1'R, 3"S, 5R, 6S)-6-(1'-hydroxyethyl)-2-(3"-tetrahydrofuranyl)-penem-3-carboxylate (43)

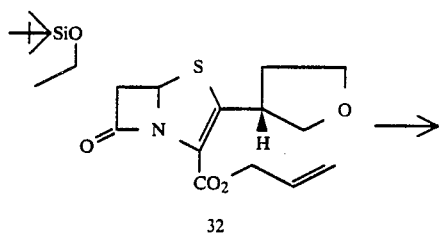

Allyl (1'R, 3"S, 5R, 6S)-6-(1'-tert-butyldimethylsilyloxyethyl)-2-(3"-tetrahydrofuranyl)penem-3-carboxylate (32) (0.200 g, 0.45 mmole), acetic acid (0.228 ml) and tetra-n-butylammonium fluoride (1.36 ml of a 1M solution in tetrahydrofuran) were subjected to the same procedure as described in Example 15 to give 0.181 g (89%) of the subject compound (48).

EXAMPLE 27

Allyl (1'R, 3"R, 5R, 6S)-6-(1'-hydroxyethyl)-2-(3"-tetrahydrofuranyl)-penem-3-carboxylate (44)

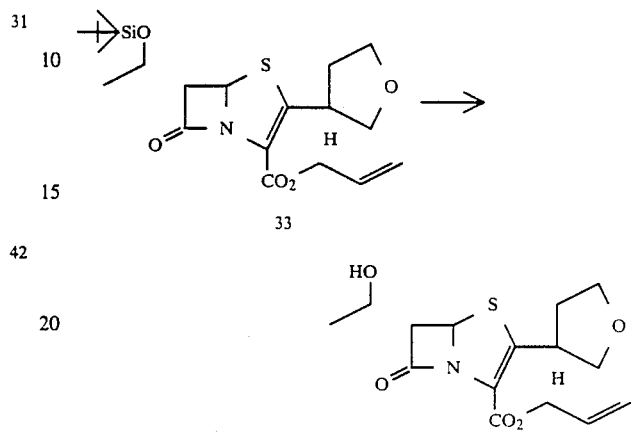

Allyl (1'R, 3"R, 5R, 6S)-6-(1'-tert-butyldimethylsilyloxyethyl)-2-(3"-tetrahydrofuranyl)penem-3-carboxylate (33) (0.200 g, 0.45 mmole), acetic acid (0.228 ml) and tetra-n-butylammonium fluoride (1.86 ml of a 1M solution in tetrahydrofuran) were subjected to the same procedure as described in Example 15 to give 0.149 g of the subject compound (44).

EXAMPLE 28

Allyl (1'R, 2"S, 5R, 6S)-6-(1'-hydroxyethyl)-2-(2"-tetrahydropyranyl)-penem-3-carboxylate (45)

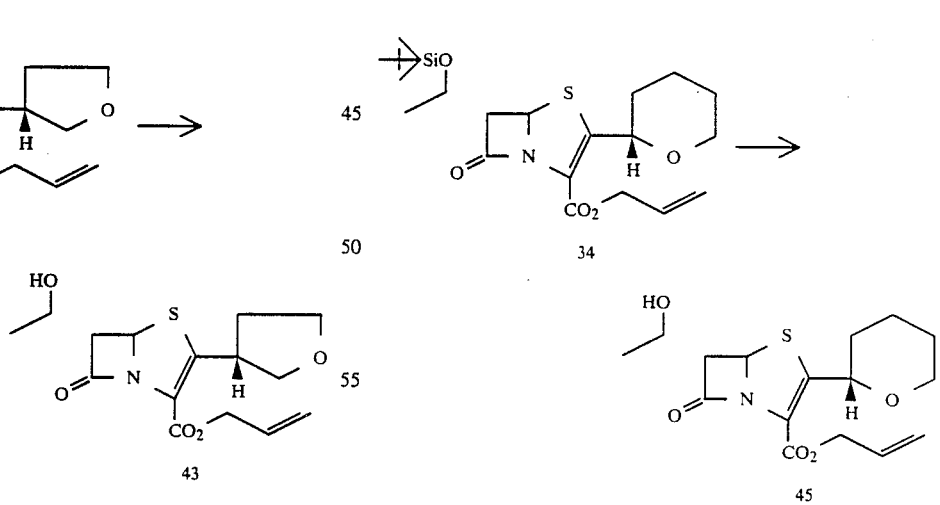

Allyl (1'R, 2"S, 5R, 6S)-6-(1'-tert-butyldimethylsilyloxyethyl)-2-(2"-tetrahydropyranyl)penem-3-carboxylate (34) (0.189 g, 0.42 mmole), acetic acid (0.21 ml) and tetra-n-butylammonium fluoride (1.25 ml of a 1M in tetrahydrofuran) were subjected to the same procedure as described in Example 15 to give 0.181 g (92%) of the subject compound (45).

EXAMPLE 29

Allyl (1'R, 2"R, 5R, 6S)-6-(1'-hydroxyethyl)-2-(2"-tetrahydropyranyl)-penem-3-carboxylate (46)

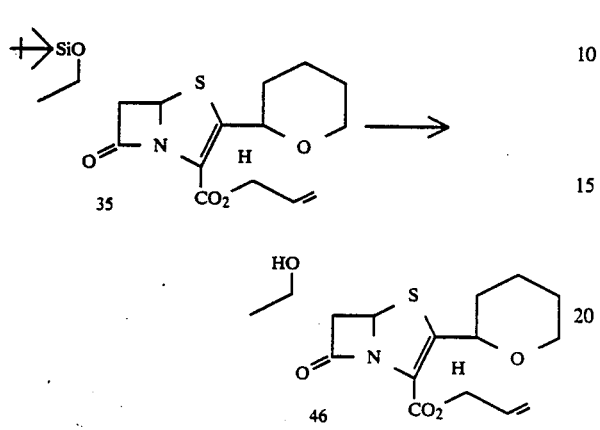

Allyl (1'R, 2"R, 5R, 6S)-6-(1'-tert-butyldimethyl-silyloxyethyl)-2-(2"-tetrahydropyranyl)penem-3-carboxylate (35) (0.194 g, 0.428 mmole), acetic acid (0.21 ml) and tetra-n-butylammonium fluoride (1.28 ml of a 1M solution in tetrahydrofuran) were subjected to the same procedure as described in Example 15 to give 0.133 g (92%) of the subject compound (46).

EXAMPLE 30

Allyl (1'R, 2"S, 5R, 6S and 1'R, 2"R, 5R, 6S)-6-(1'-hydroxyethyl)-2-(2"-para-dioxanyl)penem-3-carboxylate (47)

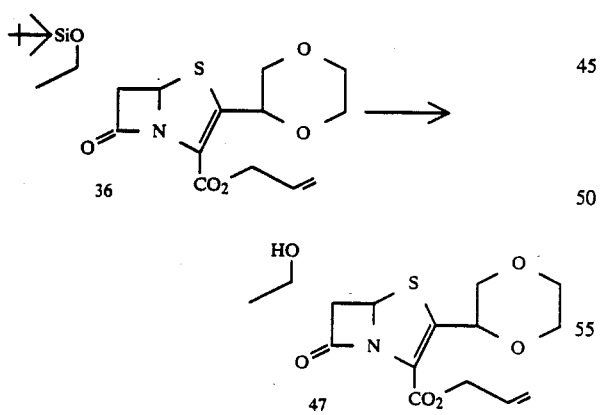

Allyl (1'R, 2"S, 5R, 6S and 1'R, 2"R, 5R, 6S)-6-(1'-tert-butyldimethylsilyloxyethyl)-2-(2"-para-dioxanyl)-penem-3-carboxylate (36) (0.168 g, 0.358 mmole), acetic acid (0.179 ml) and tetra-n-butylammonium fluoride (1.07 ml of a 1M solution in tetrahydrofuran) were subjected to the same procedure as described in Example 15 to give 0.120 g (98%) of the subject compound (47).

EXAMPLE 31

Allyl (1'R, 2"S, 5R, 6S)-6-(1'-hydroxyethyl)-2-(2"-para-dioxanyl)penem-3-carboxylate (48)

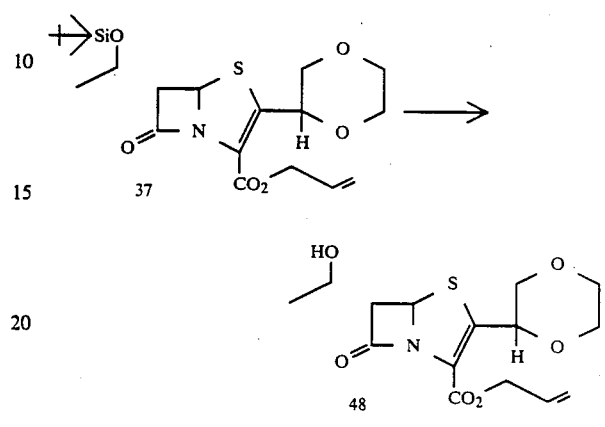

Allyl (1'R, 2"S, 5R, 6S)-6-(1'-tert-butyldimethyl-silyloxyethyl)-2-(2'-para-dioxanyl)penem-3-carboxylate (37) (0.165 g 0.361 mmole), acetic acid (0.18 ml) and tetra-n-butylammonium fluoride (1.08 ml of a 1M solution in tetrahydrofuran) were subjected to the same procedure as described in Example 15 to give 0.109 g (88%) of the subject compound (48).

EXAMPLE 32

Allyl (1'R, 2"R, 5R, 6S)-6-(1'-hydroxyethyl)-2-(2"-para-dioxanyl)penem-3-carboxylate (49)

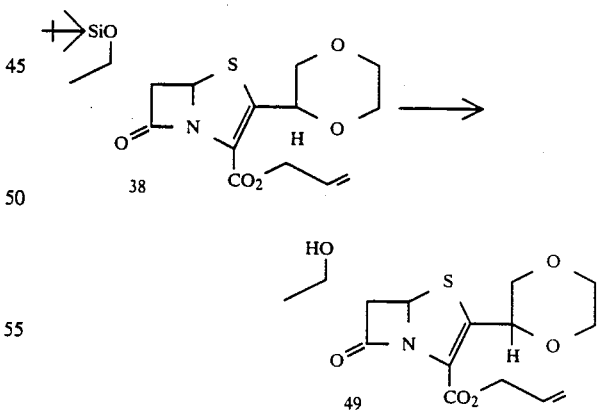

Allyl (1'R, 2"R, 5R, 6S)-6-(1'-tert-butildimethyl-silyloxyethyl)-2-(2"-para-dioxanyl)penem-3-carboxylate (38) (0.154 g, 0.339 mmole), acetic acid (0.17 ml) and tetra-n-butylammonium fluoride (1.02 ml of a 1M solution in tetrahydrofuran) were subjected to the same procedure as described in Example 15 to give 0.111 g (95.7%) of the subject compound (49).

EXAMPLE 33

Allyl (1'R, 2"R, 5R, 6S)-6-(1'-hydroxyethyl)-2-[2"-(5"-oxo)oxolanyl]penem-8-carboxylate (50)

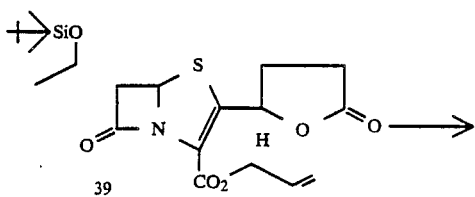

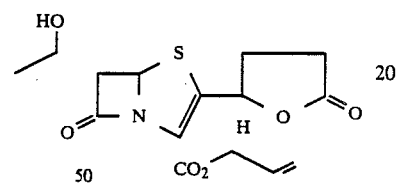

Allyl (1'R, 2"R, 5R, 6S)-6-(1'-tert-butyldimethylsilyloxyethyl)-2-[2"-(5"-oxo)oxolanyl]penem-3-carboxylate (39) (23 mg, 0.05 mmole), acetic acid (0.035 ml) and tetra-n-butylammonium fluoride (0.21 ml of a 1M solution in tetrahydrofuran) were subjected to the same procedure as described in Example 15 to give 13 mg (76%) of the subject compound (50).

EXAMPLE 34

Allyl (1'R, 2"R, 5S, 6R)-6-(1'-hydroxyethyl)-2-[2"-(5"-oxo)oxolanyl]penem-3-carboxylate (51).

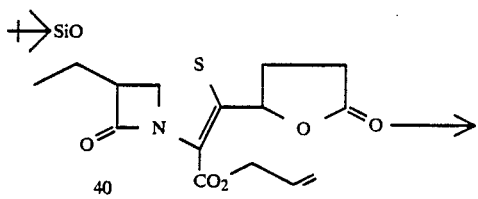

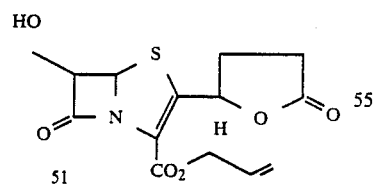

Allyl (1'R, 2"R, 5S, 6R)-6-(1'-tert-butyldimethylsilyloxyethyl)-2-[2"-(5"-oxo)oxolanyl]penem-3-carboxylate (40) (30 mg, 0.066 mmole), acetic acid (0.35 μl) and tetra-n-butylammonium fluoride (0.5 ml of a 1M solution in tetrahydrofuran) were subjected to the same procedure as described in Example 15 to give 15 mg (67%) of the subject compound (51).

EXAMPLE 35

Allyl (1'R, 2"R, 3S, 4R and 1'R, 2"S, 3S, 4R and 1'S, 2"R, 3R, 4S and 1'S, 2"S, 3R, 4S)-6-(1'-hydroxyethyl)-2-(2"'-tetrahydrofuranyl)-penem-3-carboxylate (52).

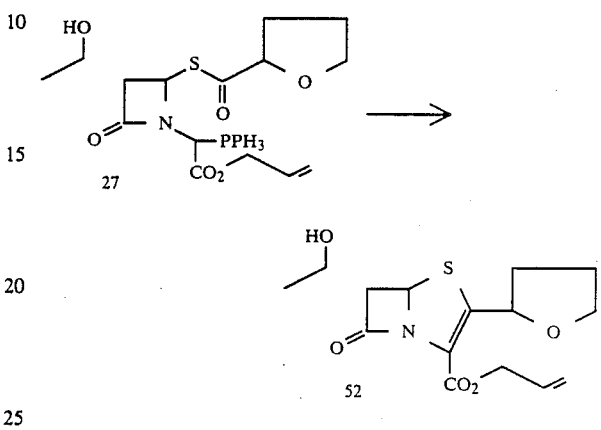

A mixture of (1'R, 2'''R, 3S, 4R and 1''R, 2'''S, 3S, 4R and 1''S, 2'''R, 3R, 4S and 1''S, 2'''S, 3R, 4S)-1-(1'-allyloxycarbonyl-2'-triphenylphosphoranilydenemethyl)-3-(1''-hydroxyethyl)-4-(2'''-tetrahydrofuranoylthio)-2-azetidinone (27) (0.666 mg, 1.10 mmole) and toluene (70 ml) was subjected to the same procedure as described in Example 16 to give 346 mg (97%) of the subject compound (52).

EXAMPLE 36

Allyl (1'R, 2"R, 5R, 6S)-6-(1'-hydroxyethyl)-2-(2"-tetrahydrofuranyl)-penem-3-carboxylate (42).

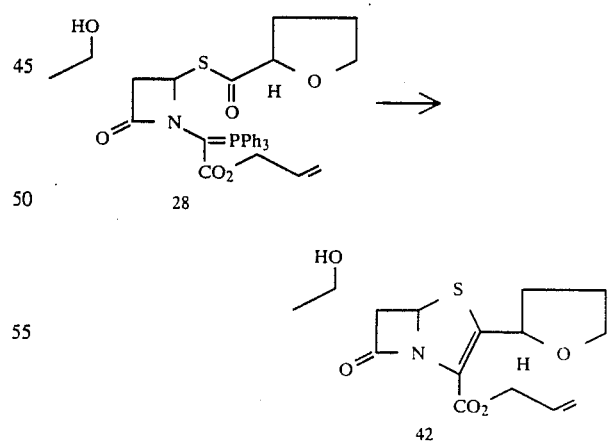

A mixture of (1"R, 2'''R, 3S, 4R)-1-(1'-allyloxycarbonyl-2'-triphenylphosphoranilydenemethyl)-3-(1''-hydroxyethyl)-4-(2'''-tetrahydrofuranoylthio)-2-azetidinone (28) (1.03 g, 1.71 mmole) and toluene (100 ml) was subjected to the same procedure as described in Example 16 to give 0.500 g (91%) of the subject compound (42).

EXAMPLE 37

Allyl (1'R, 2"S, 5R, 6S)-6-(1'-hydroxyethyl)-2-[2'''-(5'''-oxo)oxolanyl]penem-3-carboxylate (58) and allyl (1'S, 2"S, 5S, 6R)-6-(1'-hydroxyethyl)-2-[2'''-(5'''-oxo)oxolanyl]penem-3-carboxylate (54).

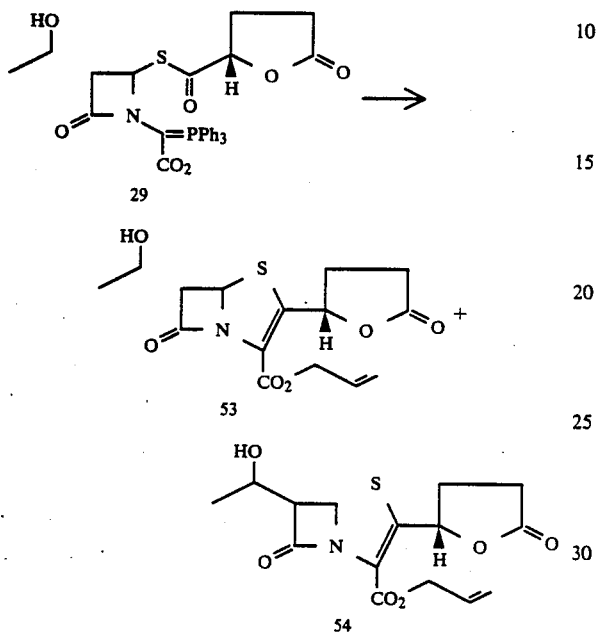

A mixture of (1'''R, 2''''S, 3R, 4S and 1'''S, 2''''S, 3S, 4R)-1-(1'-allyloxycarbonyl-2'-triphenylphosphoranilydenemethyl)-3-(1''-hydroxyethyl)-4-[2'''-(5'''-oxo)oxolanylthio]-2-azetidinone (29) (0.060 g) and toluene (20 ml) was subjected to the same procedure as described in Example 16 to give 10 mg (30%) of the subject compound (53) and 5 mg (15%) of the subject compound (54).

| Example No | Comp'd. No. | Reaction time, hr. | Yield % | IR$^{film}_{max}$ (cm$^{-1}$) Alcohol (OH) | Lactam C=O | Ester C=O |
|---|---|---|---|---|---|---|
| 35 | 52 | 10 | 66 | 3440 | 1788 | 1708 |
| 24 | 41 | 72 | 86 | 3460 | 1786 | 1713 |
| 25 | 42 | 22 | 100 | 3470 | 1796 | 1705 |
| 26 | 43 | 15.5 | 89 | 3350 | 1786 | 1704 |
| 27 | 44 | 15.5 | 100 | 3400 | 1798 | 1707 |
| 28 | 45 | 18 | 92 | 3410 | 1785 | 1710 |
| 29 | 46 | 18 | 98 | 3475 | 1788 | 1710 |
| 30 | 47 | 16 | 98 | 3380 | 1788 | 1708 |
| 31 | 48 | 16 | 88 | 3455 | 1795 | 1718 |
| 32 | 49 | 16 | 96 | 3460 | 1798 | 1718 |
| 33 | 50 | 16 | 76 | | | |
| 34 | 51 | 16 | 67 | | | |
| 37 | 53 | 16 | 30 | | | |
|    | 54 | 16 | 15 | | | |

| Comp'd. No. | NMR Spectrum Data δ (CDCl$_3$) |
|---|---|
| 46 | 1.85(1H,d,J=6.6Hz,2'-position-CH$_3$), 1.44–1.97(6H,m), 3.47–3.55(1H,m), 3.70(1H,d,d,J=1.98Hz,6.6Hz,6-position-H), 3.99–4.03(1H,m), 4.22(1H,d,J=6.6Hz,6.6Hz,1'-position-H), 4.61–4.81(2H,m,OCH$_2$CH=), 5.02 (1H,br.d.2"-position-H), 5.22–5.47(2H,m,CH=CH$_2$), 5.54(1H,d,J=1.98Hz,5-position-H), 5.88–6.02(1H,m, CH=CH$_2$) |
| 48 | 1.36(3H,d,J=5.94Hz,2'-position-CH$_3$), 3.30–4.02(7H,m), 4.23(1H,d,q,J=5.94Hz,6.6Hz,1'-position-H), 4.62–4.86 (2H,m,OCH$_2$CH=), 5.23–5.48(3H,m), 5.60(1H,d, J=1.98Hz,5-position-H), position-H), 5.87–6.08(1H,m,CH=CH$_2$) |
| 49 | 1.35(3H,d,J=6.60Hz,2'-position-CH$_3$), 3.41–3.99(7H,m), 4.28(1H,d,q,J=6.60Hz,6.60Hz,1'-position-H), 4.61–4.85 (2H,m,—OCH$_2$CH=), 5.23–5.47(3H,m), 5.55(1H,d,J= 1.31Hz, 5-position-H), 5.88–6.03(1H,m,—CH=CH$_2$) |
| 50 | 1.35(3H,d,J=7.0Hz,2'-position-CH$_3$), 2.0–2.8(4H,m), 3.79 (1H,d,d,J=2Hz,6Hz,6-position-H), 4.23(1H,q,J=7Hz,1'-position-H), 4.65 and 4.78(for each, 1H,d,d,J=6Hz,13Hz, OCH$_2$CH=), 5.28(1H,d,J=11Hz,CH=CH$_2$), 5.41(1H, d,d,J=2Hz, 17Hz,CH=CH$_2$), 5.62(1H,d,J=2Hz,5-position-H), 5.9–6.0 (1H,m,CH=CH$_2$), 6.01(1H,t,J= 7Hz,2"-position-H). |
| 51 | 1.35(3H,d,J=7.0Hz,2'-position-CH$_3$), 2.0–2.8(4H,m), 3.79 (1H,d,d,J=2Hz,6Hz,6-position-H), 4.23(1H,q,J=7Hz,1'-position-H), 4.65 and 4.78(for each, 1H,d,d,J=6Hz,13Hz, OCH$_2$CH=), 5.28(1H,d,J=11Hz,—CH=CH$_2$), 5.41 (1H,d,d,J=2Hz, 17Hz,CH=CH$_2$), 5.62(1H,d,J=2Hz, 5-position-H), 5.9–6.0 (1H,m,CH=CH$_2$), 6.01(1H,t, J=7Hz,2"-H) |
| 52 | 1.36(3H,d,J=6Hz,2"-position-CH$_3$), 1.60–2.09(4H,m), 2.35 (1H,m), 3.71(1H,d,d,J=8Hz,6-position-H), 3.76–4.02 (2H,m), 4.16–4.30(1H,m,1'-position-H), 4.58–5.90(2H, m,—OCH$_2$—CH=), 5.26(1H,d,d,J=11Hz, —CH=CH$_2$), 5.30–5.48(2H,m,CH=CH$_2$ and 2"-position-H), 5.51(0.6H,d,J=1.6Hz,5-position-H), 5.58 (0.4H,d,J=1.7Hz,5-position-H), 5.87–6.03(1H,m, —CH=CH$_2$). |
| 41 | 1.36(3H,d,J=6Hz,2'-position-CH$_3$), 1.60–2.09(4H,m), 2.35–2.50(1H,m), 3.71(1H,d,d,J=8Hz,6-position-H), 3.76–4.01(2H,m), 4.16–4.43(1H,m,1'-position-H), 4.66 and 4.76(for each, 1H,d,d,J=5Hz,14Hz,O—CH$_2$CH=), 5.26(1H, d,d,J=11Hz,CH=CH$_2$), 5.34–5.48(2H,m,CH=CH$_2$ and H O 5.58(1H,d,J=1.7Hz,5-position-H), 5.87–6.03(1H,m,CH=CH$_2$) |
| 42 | 1.35(3H,d,J=7Hz,2'-position-CH$_3$), 1.75–2.08(4H,m), 2.40–2.52(1H,m), 3.72(1H,d,d,J=8Hz,6-position-H), 3.81–3.89(1H,m), 3.94–4.02(1H,m), 4.16–4.26(1H,m,1'-position-H), 4.77 and 4.64(for each, 1H,d,d,J=18Hz,O—CH$_2$CH=), 5.26(1H,d,d,J=11Hz,—CH=CH$_2$), 5.86(1H,d,d,J=7Hz,2"-position-H), 5.41(1H,d,d,J=17Hz,CH=CH$_2$), 5.51(1H,d, J=1.6Hz,5-position-H), 5.88–6.02(1H,m,CH=CH$_2$) |
| 43 | 1.36(3H,d,J=6.6Hz,2'-position-CH$_3$), 1.79–1.98(1H,m), 2.17–2.33(1H,m), 3.64–3.87(3H,m), 3.92–4.06(2H,m), 4.17–4.35(1H,m,1'-position-H), 4.35–4.50(1H,m), 4.67- and 4.79(for each, 1H,d,d,J=5.3Hz,13Hz,OCH$_2$CH=), 5.27 (1H,d,d,J=1.3Hz,9.9Hz,CH=CH$_2$), 5.41(1H,d,d,J=1.3Hz, 17.2Hz,CH=CH$_2$), 5.55(1H,d,J=1.3Hz,5-position-H), 5.87– |

| Comp'd. No. | NMR Spectrum Data δ (CDCl₃) |
|---|---|
| | 6.05(1H,m,CH=CH₂). |
| 44 | 1.86(3H,d,J=6.6Hz,2'-position-CH₃), 1.86-2.09(1H,m), 2.26-2.43(1H,m), 3.61-3.76(2H,m), 3.76-3.88(1H,m), 3.88-4.05(2H,m), 4.16-4.31(1H,m,1'-position-H), 4.35-4.50(1H,m), 4.66 and 4.78*for each, 1H,d,d,J=5Hz,14Hz, OCH₂CH=), 5.27(1H,d,d,J=1.3Hz,10.6Hz,CH=CH₂), 5.41 (1H,d,d,J=1.3Hz,17.2Hz,CH=CH₂), 5.58(1H,d,J=2.0Hz,5-position-H), 5.88-6.05(1H,m) |
| 45 | 1.34(1H,d,J=5.94Hz,2'-position-CH₃), 1.42-1.97(6H,m), 3.71(1H,d,d,J=1.98Hz,5.34Hz,6-position-H), 3.46-3.54 (1H,m), 4.01-4.08(1H,m), 4.23(1H,d,q,J=5.34Hz,5.94Hz, 1'-position-H), 4.6204.80(2H,m,—OCH₂CH=), 5.04(1H,d,d, J=1.98Hz,8.58Hz,2"-position-H), 5.26-5.39(2H,m,CH=CH₂), 5.56(1H,d,J=1.98Hz,5-position-H), 5.87-6.02(1H,m,CH=CH₂). |
| | 1.19(3H,d,J=8Hz,2'-position-CH₃), 2.01-2.10(2H,m), 2.6-2.8(2H,m), 3.76(1H,d,d,J=2Hz,6-position-H), 4.24(1H,br.t,1'-position-H), 4.67 and 4.79(for each, 1H,d,d,J=7Hz,15Hz,—OCH₂CH=), 5.28(1H,d,d,J=8Hz,10Hz, —CH=CH₂), 5.40(1H,d,d,J=3Hz, 7Hz,—CH=CH₂), 5.66(1H,d, J=2Hz,5-position-H), 5.86-6.01(1H,m,CH—CH₂), 6.07 (1H,t,J=8Hz,2"-position-H). |

EXAMPLE 38

Potassium (1'R, 2"R, 5R, 6S and 1'R, 2"S, 5R, 6S and 1'S, 2"R, 5S, 6R and 1'S, 2"S, 5S, 6R)-6-(1'-hydroxyethyl)-2-(2"-tetrahydrofuranyl)-penem-3-carboxylate (SUN 4068) and potassium (1'R, 2"S, 5R, 6S and 1'S, 2"R, 5S, 6R)-6-(1'-hydroxyethyl)-2-(2"-tetrahydrofuranyl)-penem-8-carboxylate

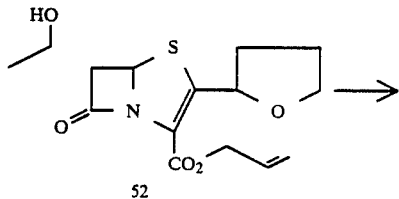

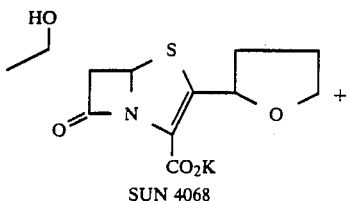

SUN 4068

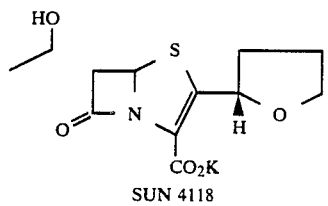

SUN 4118

In methylene chloride (0.4 ml) was dissolved a mixture of allyl (1'R, 2"R, 3S, 4R and 1'R, 2"S, 3S, 4R and 1'S, 2"R, 3R, 4S and 1'S, 2"S, 3R, 4S)-6-(1'-hydroxyethyl)-2-(2"-tetrahydrofuranyl)penem-3-carboxylate (52) (48 mg, 0.18 mmole), triphenylphosphine (33 mg) and palladium tetrakis-triphenylphosphine (3.3 mg), and potassium 2-ethylhexanoate (0.4 ml of a 0.5M in ethyl acetate) was added to the solution at room temperature under stirring. After stirring for 1 hour, acetone (2 ml) was added to the mixture, and the insoluble matter was filtered out, washed with acetone and ether successively, and dried in a desiccator under reduced pressure to give 23.5 mg (55.8%) potassium (1'R, 2"R, 5R, 6S and 1'R, 2"S, 5R, 6S and 1'S, 2"R, 5S, 6R and 1'S, 2"S, 5S, 6R)-6-(1'-hydroxyethyl)-2-(2"-tetrahydrofuranyl)-penem-3-carboxylate (SUN 4068) (a 3/1 mixture of (1'R, 2"R, 5R, 6S and 1'S, 2"S, 5S, 6R)/(1'R, 2"S, 5R, 6S and 1'S, 2"R, 5S, 6R)) in the form of a colorless powder. On the other hand, the crystals, which were obtained as the second precipitate from the filtrate, were collected by filtration, and dried in a desiccator under reduced pressure to give 3.9 mg (93%) of potassium (1'R, 2"S, 5R, 6S and 1'S, 2"R, 5S, 6R)-6-(1'-hydroxyethyl)-2-(2"-tetrahydrofuranyl)penem-3-carboxylate (SUN 4118) in the form of a colorless powder.

EXAMPLE 39-(1)

Potassium (1'R, 2"R, 5R, 6S)-6-(1'-hydroxyethyl)-2-(2"-tetrahydrofuranyl)-penem-3-carboxylate (SUN 4435)

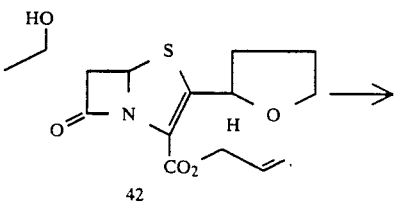

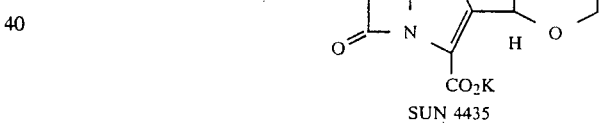

SUN 4435

Allyl (1'R, 2"R, 5R, 6S)-6-(1'-hydroxyethyl)-2-(2"-tetrahydrofuranyl)penem-3-carboxylate (42) (0.500 g, 1.54 mmole), triphenylphosphine (0.0884 g), palladium tetrakistriphenylphosphine (0.0884 g) and potassium 2-ethylhexanoate (3.1 ml) of a 0.5M solution in ethyl acetate) were subjected to the same procedure as described in Example 38 to give 96 mg (19.8%) of the subject compound (SUN 4435).

EXAMPLE 39-(2)

Sodium (1'R, 2"R, 5R, 6S)-6-(1'-hydroxyethyl)-2-(2"-tetrahydofuranyl)penem-3-carboxylate (SUN 5555).

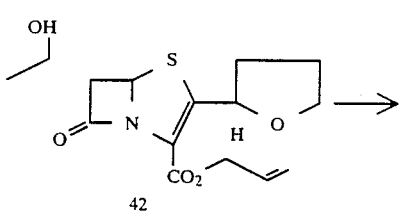

41

-continued

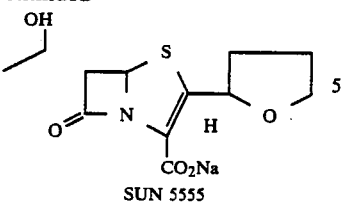
SUN 5555

Allyl (1'R, 2"R, 5R, 6S)-6-(1'-hydroxyethyl)-2-(2"-tetrahydrofuranyl)penem-3-carboxylate (42) (32 mg, 0.1 mmole), triphenylphosphine (3 mg), palladium tetrakistriphenylphosphine (3 mg) and sodium 2-ethylhexanoate (0.1 mmole) were subjected to the same procedure as described in Example 38 to give 23.6 mg (76.8%) of the subject compound (SUN 5555).

EXAMPLE 40

Potassium (1'R, 2"S, 5R, 6S)-6-(1'-hydroxyethyl)-2-(2"-tetrahydropyranyl)-penem-3-carboxylate (SUN 4740)

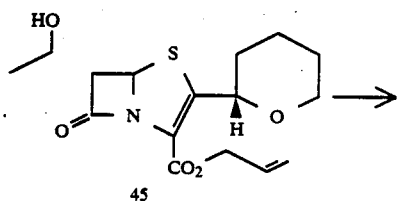
45

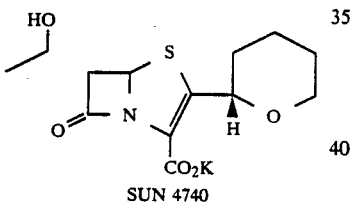
SUN 4740

Allyl (1'R, 2"S, 5R, 6S)-6-(1'-hydroxyethyl)-2-(2"-tetrahydropyranyl)penem-3-carboxylate (45) (48.7 mg, 0.144 mmole), triphenylphosphine (1 mg), palladium tetrakistriphenylphosphine (1 mg) and potassium 2-ethylhexanoate (0.28 ml of a 0.5M solution in ethyl acetate) were subjected to the same procedure as described in Example 38 to give 14.2 mg (29.2%) of the subject compound (SUN 4740).

EXAMPLE 41

Potassium (1'R, 2"R, 5R, 6S)-6-(1'-hydroxyethyl)-2-(2"-tetrahydropyranyl)-penem-3-carboxylate (SUN 4741)

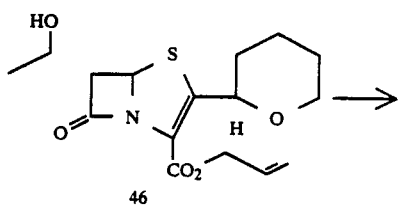
46

42

-continued

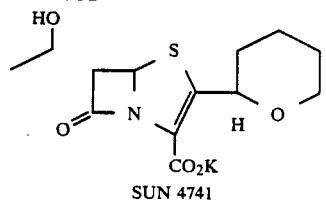
SUN 4741

Allyl (1'R, 2"R, 5R, 6S)-6-(1'-hydroxyethyl)-2-(2"-tetrahydropyranyl)penem-8-carboxylate (46) (48.8 mg), triphenylphosphine (1 mg), palladium tetrakistriphenylphosphine (1 mg) and potassium 2-ethylhexanoate (0.25 ml of a 0.5M solution in ethyl acetate) were subjected to the same procedure as described in Example 38 to give 18.8 g (31.7%) of the subject compound (SUN 4741).

EXAMPLE 42

Potassium (1'R, 2"S, 5R, 6S)-6-(1'-hydroxyethyl)-2-[2"-(5"-oxo)oxolanyl]penem-3-carboxylate (SUN 4262)

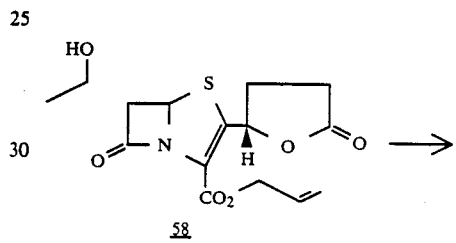
58

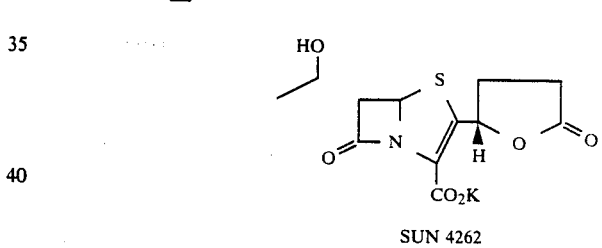
SUN 4262

Allyl (1'R, 2"S, 5R, 6S)-6-(1'-hydroxyethyl)-2-[2"-(5"-oxo)oxolanyl]penem-3-carboxylate (58) (10 mg, 0.029 mmole), triphenylphosphine (0.2 mg), palladium tetrakistriphenylphosphine (0.2 mg) and potassium 2-ethylhexanoate (0.06 ml of a 0.5M solution in ethyl acetate) were subjected to the same procedure as described in Example 38 to give 8 mg (80%) of the subject compound (SUN 4262).

EXAMPLE 43

Potassium (1'R, 2"R, 5R, 6S)-6-(1'-hydroxyethyl)-2[2"-(5"-oxo)oxolanyl]penem-3-carboxylate (SUN 4347).

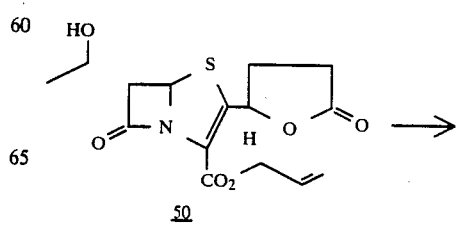
50

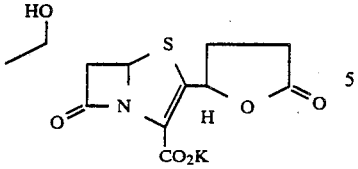

SUN 4347

Allyl (1'R, 2''R, 5R, 6S)-6-(1'-hydroxyethyl)-2-[2''-(5''-oxo)oxolanyl]penem-3-carboxylate (50) (15 mg, 0.044 mmole), triphenylphosphine (0.2 mg), palladium tetrakistriphenylphosphine (0.2 mg) and potassium 2-ethylhexanoate (0.1 ml of a 0.5M solution in ethyl acetate) were subjected to the same procedure as described in Example 38 to give 6 mg (40%) of the subject compound (SUN 4347).

EXAMPLE 44

Potassium (1'R, 2''R, 5S, 6R)-6-(1'-hydroxyethyl)-2[2''-(5''-oxo)oxolanyl]penem-3-carboxylate (SUN4325).

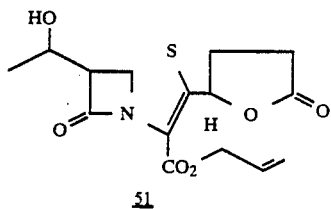

51

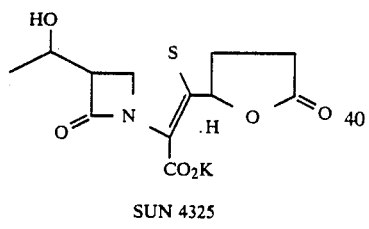

SUN 4325

Allyl (1'R, 2''R, 5S, 6R)-6-(1'-hydroxyethyl)-2-[2''-(5''-oxo)oxolanyl]penem-3-carboxylate (51) (4.9 mg, 0.015 mmole), triphenylphosphine (0.1 mg), palladium tetrakistriphenylphosphine (0.1 mg) and potassium 2-ethylhexanoate (0.004 ml of a 0.5 M solution in ethyl acetate) were subjected to the same procedure as described in Example 38 to give 2.7 mg (55%) of the subject compound (SUN 4325).

EXAMPLE

Potassium (1'R, 2''S, 5R, 6S)-6-(1'-hydroxyethyl)-2-(2''-tetrahydofuranyl)penem-3-carboxylate (SUN 4434)

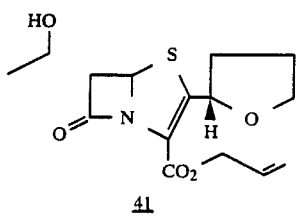

41

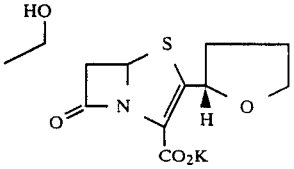

SUN 4484

A mixture of (1'R, 2''S, 5R,6S)-6-(1'-hydroxyethyl)-2-(2''-tetrahydrofuranyl)penem-3-carboxylate (41) (20 mg, 0.061 mmole). and palladium tetrakistrisphenylphosphine (1.4 mg) was dissolved in tetrahydrofuran (0.8 ml), and tri-n-butyltin hydride (20 μl) was added to the solution at −10° C. under stirring. 25 minutes later, acetic acid (4 μl) was added to the mixture, followed by stirring for another 10 minutes. The reaction solution was concentrated under reduced pressure, and the residue was treated with water (3 ml) and ethyl acetate (2 ml). 2M potassium hydrogencarbonate was added dropwise to the mixture under stirring to adjust it to pH 8.1. The organic layer was extracted three times with water, and the water layers were combined and washed with ethyl acetate. The water layer was lyophilized, and the resulting residue was purified by column chromatography utilizing XAD-2 (9 ml) to give 8.8 mg (44%) of the subject compound (SUN 4434) in the form of a colorless powder.

EXAMPLE 46

Potassium (1'R, 2''R, 5R, 6S)-6-(1'-hydroxyethyl)-2-(2''-tetrahydrofuranyl)-penem-3-carboxylate (SUN 4435)

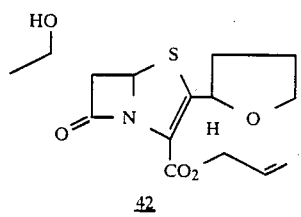

42

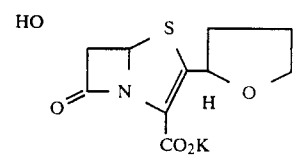

SUN 4435

Allyl (1'R, 2''R, 5R, 6S)-6-(1'-hydroxyethyl)-2-(2''-tetrahydrofuranyl)penem-3-carboxylate (42) (0.877 g, 2.70 mmole), palladium tetrakistriphenylphosphine (62 mg), tri-n-butylthin hydride (0.87 ml) and acetic acid (0.18 ml) were subjected to the same procedure as described in Example 45 to give 0.330 g (38%) of the subject compound (SUN 4435).

EXAMPLE 47

Potassium (1'R, 3''S, 5R, 6S)-6-(1'-hydroxyethyl)-2-(11-tetrahydrofuranyl)penem-3-carboxylate (SUN 4725)

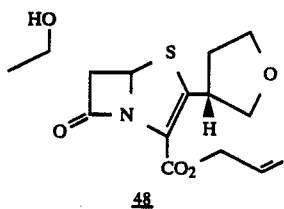

<u>48</u>

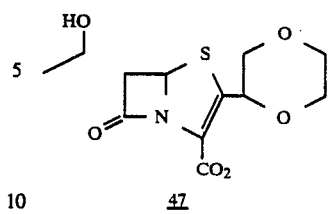

<u>47</u>

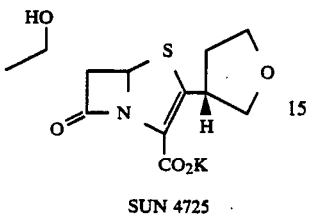

SUN 4725

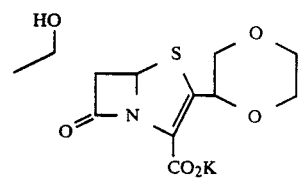

SUN 4742

Allyl (1'R, 3"S, 5R, 6S)-6-(1'-hydroxyethyl)-2-(3"-tetrahydrofuranyl)penem-3-carboxylate (43) (80 mg, 0.25 mmole), palladium tetrakistrisphenylphosphine (5.6 mg), tri-n-butyltin hydride (0.079 ml) and acetic acid (17 μl) were subjected to the same procedure as described in Example 45 to give 51 mg (64%) of the subject compound (SUN 4725).

EXAMPLE 48

Potassium (1'R, 3"R, 5R, 6S)-6-(1'-hydroxyethyl)-2-(3"-tetrahydrofuranyl)-penem-3-carboxylate (SUN 4726)

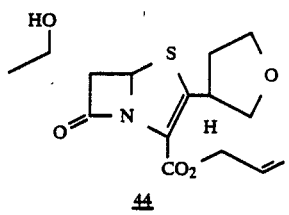

<u>44</u>

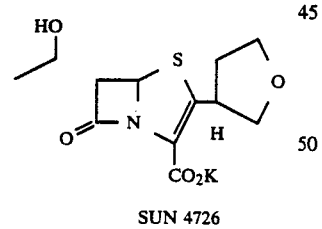

SUN 4726

Allyl (1'R, 3"R, 5R, 6S)-6-(1'-hydroxyethyl)-2-(3"-tetrahydrofuranyl)penem-3-carboxylate (44) (80 mg, 0.25 mmole), palladium tetrakistriphenylphosphine (5.6 mg), tri-n-butyltin hydride (0.079 ml) and acetic acid (17 μl) were subjected to the same procedure as described in Example 45 to give 60 mg (75%) of the subject compound (SUN 4726).

EXAMPLE 49

Potassium (1'R, 2"s, 5R, 6S and 1'R, 2"R, 5R, 6S)-6-(1'-hydroxyethyl)-2-(2"-paradioxanyl)penem-3-carboxylate (SUN 4742).

Allyl (1'R, 2"S, 5R, 6S and 1'R, 2"R, 5R, 6S)-6-(1'-hydroxyethyl)-2-(3"-tetrahydrofuranyl)penem-3-carboxylate (47) (85 mg, 0.249 mmole), palladium tetrakistriphenylphosphine (5.4 mg), tri-n-butyltin hydride (78 μl) and acetic acid (16.2 μl) were subjected to the same procedure as described in Example 45 to give 14 mg (16.6%) of the subject compound (SUN 4742).

EXAMPLE 50

Potassium (1'R, 2"S, 5R, 6S)-6-(1'-hydroxyethyl)-2-(2"-para-dioxanyl)penem-3-carboxylate (SUN 4770)

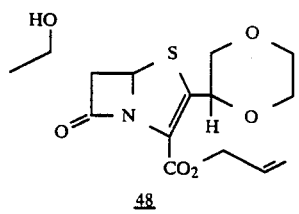

<u>48</u>

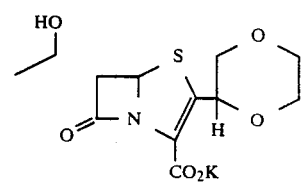

SUN 4770

Allyl (1'R, 2"S, 5R, 6S)-6-(1'-hydroxyethyl)-2-(2"-paradioxanyl)penem-3-carboxylate (48) (108.8 mg, 0.318 mmole), palladium tetrakistriphenylphosphine (6.9 mg), tri-n-butyltin hydride (100 μl) and acetic acid (20.7 μl) were subjected to the same procedure as described in Example 45 to give 77 mg (71.8%) of the subject compound (SUN 4770).

EXAMPLE 51

Potassium (1'R, 2"R, 5R, 6S)-6-(1'-hydroxyethyl)-2-(2"-para-dioxanyl)penem-3-carboxylate (SUN 4771)

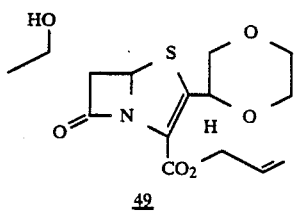

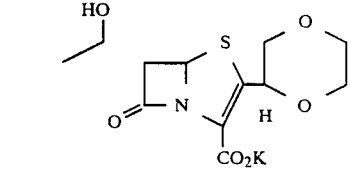

SUN 4771

Allyl (1'R, 2"R, 5R, 6S)-6-(1'-hydroxyethyl)-2-(2"-para-dioxanyl)penem-3-carboxylate (49) (110.7 mg, 0.324 mmole), palladium tetrakistriphenylphosphine (7 mg), tri-n-butyltin hydride (0.101 ml) and acetic acdi (21 μl) were subjected to the same procedure as described in Example 45 to give 59 mg (53.4%) of the subject compound (SUN 4771).

| Example No. | SUN No. | Yield % | $[\alpha]_D^{22°}$ | IR$_{max}^{KBr}$ (cm$^{-1}$) Alcohol (OH) | Lactam C = O |
|---|---|---|---|---|---|
| 58 | 4068 | 55.8 | | 3400 | 1770 |
|  | 4118 | 9.8 | | 3265 | 1779 |
| 47 | 4434 | 44.0 | +119.5° (C. = 1.267) | 3320 | 1778 |
| 39 | 4435 | 19.8 | +116.4° (C. = 1.127) | 3345 | 1770 |
| 46 |  | 38.0 | | | |
| 47 | 4725 | 64.0 | +97.7° (C. = 1.027) | 3380 | 1776 |
| 48 | 4726 | 75.0 | +58.8° (C. = 0.29) | 3340 | 1764 |
| 40 | 4740 | 29.2 | +89.2° (C. = 0.12) | 3210 | 1760 |
| 41 | 4741 | 31.7 | +86.0° (C. = 0.10) | 3195 | 1745 |
| 49 | 4742 | 16.6 | | | |
| 50 | 4770 | 71.8 | +62.0° (C. = 0.51) | 3400 | 1778 |
| 51 | 4771 | 53.4 | +73.7° (C. = 0.51) | 3410 | 1770 |
| 42 | 4262 | 30.0 | | 3400 | 1775 |
| 43 | 4374 | 40.0 | +57.0° (C. = 0.13) | 3380 | 1790 |
| 44 | 4325 | 55.0 | +60.0° (C. = 0.10) | 3400 | 1785 |
| 39 | 5555 | 76.8 | +60.0° (C. = 0.10) | 3345 | 1770 |

| SUN No. | NMR Spectrum Data δ (D$_2$O) |
|---|---|
| 4068 | 1.18 (3H,d,J=6Hz,2'-position-CH$_3$), 1.61-1.99(8H,m), 2.09-2.30(1H,m), 3.63-3.86(3H,m), 4.01-4.18(H,m,1'-position-H) 5.47(0.75H,d,5-position-H), 5.49(0.25H,d,5-position-H) |
| 4118 | 1.15(3H,d,J=7.5Hz,2'-position-CH$_3$), 1.59-1.99(3H,m), 2.08-2.28(1H,m), 3.63-3.86(3H,m), 4.03-4.16(1H,m,1'-position-H), 5.40(1H,t,J=8Hz,2'-position-H), 5.46(1H,d,d,5-position-H) |
| 4434 | 1.18(3H,d,J=6Hz,2'-position-CH$_3$), 1.62-1.97(3H,m), 2.12-2.27(1H,m), 3.67-3.89(3H,m), 4.05-4.18(1H,m,1'-position-H), 5.43(1H,d,d,J=7Hz,2"-position-H), 5.49(1H,d,J=1.3Hz,5-position-H) |
| 4435 | 1.18(3H,d,J=6Hz,2'-position-CH$_3$), 1.07-2.04(3H,m), 2.18-2.34(1H,m), 3.67-3.90(3H,m), 4.05-4.17(1H,m,1'-position-H), 5.39(1H,d,d,J=7Hz,2"-position-H), 5.47(1H,d,5-position-H). |
| 4725 | 1.18(3H,d,2'-position-CH$_3$), 1.67-1.84(1H,m), 2.06-2.25 (1H,m), 3.58-3.95(5H,m), 4.05-4.23(1H,m,1'-position-H), 4.23-4.45(1H,m), 5.49(1H,d,5-position-H) |
| 4726 | 1.18(3H,d,2'-position-CH$_3$), 1.80-2.03(1H,m), 2.13-2.32 (1H,m), 3.51-4.05(5H,m), 4.05-4.23(1H,m,1'-position-H), 4.23-4.45(1H,m), 5.49(1H,d,5-position-H). |
| 4740 | 17(3H,d,J=6.6Hz,2'-position-CH$_3$), 1.14-1.80(6H,m), 3.47 (1H,d,J=6.6Hz,6-position-H), 3.86(1H,d), 4.11(1H,d,q,J= 6.6Hz,6.6Hz,1'-position-H), 5.12(1H,d,J=10.53,2"-position-H), 5.48(1H,d,5-position-H). |
| 4741 | 1.16(3H,d,J=6.6Hz,2'-position-CH$_3$), 1.36-1.79(6H,m), 3.44 (1H,m), 3.74(1H,d,d,J=1.32Hz,5.9Hz,6-position-H), 3.84 (1H,br.d.), 4.09(1H,d,q,J=5.9Hz,6.6Hz,1'-position-H), 5.02-5.10(1H,m), 5.48(1H,d,J=1.32Hz,5-position-H) |
| 4770 | 1.17(3H,d,J=6.59Hz,2'-position-CH$_3$), 3.36-3.85(7H,m),4.11 (1H,d,q,J=5.88Hz,6.59Hz,1'-position-H), 5.32(1H,d,d,J= 2.33Hz,9.7Hz,2"-position-H), 5.52(1H,d,5-position-H) |
| 4771 | 1.17(3H,d,J=6.60Hz,2"-position-CH$_3$), 3.43-3.89(7H,m), 4.10(1H,d,J=6.6Hz,1'-position-H), 5.32(1H,d,d,J=9.9Hz,2"-position-H), 5.50(1H,d,5-position-H) |
| 4262 | 1.2(3H,d,J=7Hz,2'-position-CH$_3$), 2.0-2.8(4H,m), 3.87 (1H,d,J=7Hzm6-position-H), 4.16(1H,qunit.J=7Hz,1'- |

| SUN No. | NMR Spectrum Data δ (D₂O) |
|---|---|
| | position-H), 5.60(H,s,5-position-H), 6.24(1H,t,J=8Hz, 2″-position-H) |
| 4374 | 1.18(3H,d,J=7Hz,2′-position-CH₃), 2.1–2.3 and 2.5–2.7 (4H,m), 3.81(1H,d,J=1Hz,6-position-H), 4.12(1H,quint. J=7Hz,1′-position-H), 5.57(1H,d,J=1Hz,6-position-H), 6.16(1H,t,J=7Hz,2″-position-H) |
| 4325 | 1.2(3H,d,J=7Hz,2′-position-CH₃), 2.0–2.8(4H,m), 3.87 (1H,d,J=7Hz,6-position-H), 4.16(1H,quint.J=7Hz,1′1 position-H), 5.60(1H,s,5-position-H), 6.24(1H,t,J=8Hz, 2″-position-H) |

By carrying out consecutively the same procedure as described in Examples 4-(2), 13 and 15, there were synthesized the following compounds from 1-(1-allyloxycarbonyl-2-triphenylphosphoranilydenemethyl)-3-(1″-tert-butyldimethylsilyloxyethyl)-4-silver-thio-2-azetidinone:

REFERENCE EXAMPLE 1

Allyl (1′R, 5R, 6S and 1′S, 5S, 6R)-2-(2″-furanyl)-6-(1′-hydroxyethyl)penem-3-carboxylate (55).

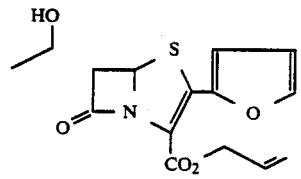

55

REFERENCE EXAMPLE 2

Allyl (1′R, 5R, 6S and 1′S, 6R)-2-(3″-furanyl)-6-(1′,-hydroxyethyl)penem-3-carboxylate (56)

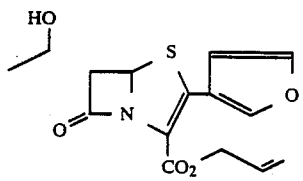

56

REFERENCE EXAMPLE 3

Allyl (1′R, 5R, 6S and 1′S, 5S, 6R)-6-(1′-hydroxyethyl)-2-(methoxymethyl)penem-3-carboxylate (57)

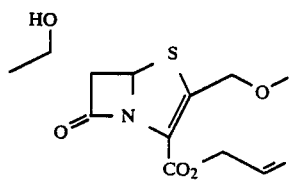

57

REFERENCE EXAMPLE 4

Allyl (1′R, 5R, 6S and 1′S, 5S, 6R)-2-(ethoxymethyl)-6-(1′-hydroxyethyl)penem-3-carboxylate (58)

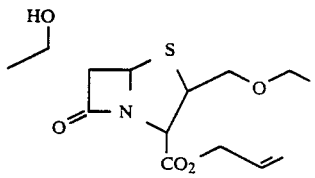

58

REFERENCE EXAMPLE 5

Allyl (1 ′R, 5R, 6S and 1′S, 5S, 6R)-2-(ethylthiomethyl)-6-(1′-hydroxyethyl)penem-3-carboxylate (59)

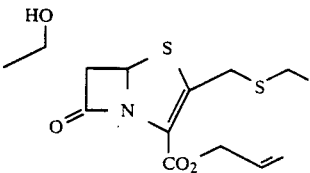

59

REFERENCE EXAMPLE 6

Allyl (1 ′R, 5R, 6S and 1′,S, 5S, 6R)-6-(1-hydroxyethyl)-2-(3″-thiophenemethyl)penem-3-carboxylate (60)

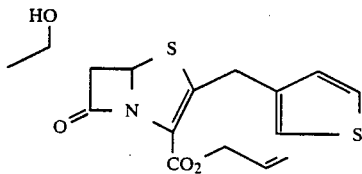

60

| Reference Example No. | Comp'd. No. | Spectrum Data |
|---|---|---|
| 1 | 55 | IR$_{max}^{KBr}$ (cm⁻¹): 3425, 1770, 1705 NMR (CdCl₃)δ: 1.39(3H,d,J=6.3Hz), 3.75(1H, dd,J=1Hz,6.8Hz), 4.21–4.87(1H,m), 4.70 and |

-continued

| Reference Example No. | Comp'd. No. | Spectrum Data |
|---|---|---|
| | | 4.82(AB type d,d,J=5Hz,14Hz), 5.27(1H,dd, J=9.9Hz), 5.43(1H,dd,J=17.2Hz), 5.90–6.08 (1H,m), 6.55(1H,dd,J=1.7Hz,8.6Hz), 7.58(1H, d,J=1.7Hz), 7.69(1H,d,J=8.6Hz) |
| 2 | 56 | $IR_{max}^{KBr}$ (cm$^{-1}$): 3410, 1775, 1705 NMR (CDCl$_3$)δ: 1.39(3H,d,J=6.6Hz), 3.75(1H, dd,J=1.3Hz,6.8Hz), 4.21–4.38(1H,m), 5.25 (1H,dd,J=1.8Hz,10.4Hz), 5.40(1H,dd,J=1.3Hz, 17.2Hz), 5.60(1H,d,J=1.8Hz), 5.88–6.06(1H,m), 7.79(1H,d,J=2Hz), 7.43(1H,d,J=2Hz), 8.06(1H,s) |
| 3 | 57 | NMR (CDCl$_3$)δ: 1.18(3H,d,J=7Hz), 3.41(3H,s), 3.76(1H,dd,J=3Hz,6Hz), 4.28(1H,m), 4.58 and 4.68(2H,AB type), 4.7–4.8(2H,m), 5.2–5.4(2H, m), 5.62(1H,d,J=3Hz), 5.8–6.2(1H,m) $IR_{max}^{KBr}$ (cm$^{-1}$): 1790, 1710 |
| 4 | 58 | NMR (CDCl$_3$)δ: 1.22(3H,t,J=7Hz), 1.35(8H,d,J= 6Hz), 3.56(2H,q,J=7Hz), 3.73(1H,dd=2Hz,6H$_2$), 4.23(1H,m), 4.59 and 4.75 (AB type)4.67, 4.60– 4.68(2H,m), 5.28(1H,d,J=10Hz), 5.40(1H,d,J=6Hz), 5.59(1H,d.J=1Hz), 5.88–6.01(1H,m) |
| 5 | 59 | NMR (CDCl$_3$)δ: 1.26(3H,t,J=7Hz), 1.35(3H,d,J= 6Hz), 2.57(2H,q,J=7Hz), 3.73(1H,d,J=5Hz), 8.84 and 4.05(AB type), 4.24(1H,m), 4.67(1H,dd,J= 6Hz,13Hz), 4.76(1H,dd,J=6Hz,13Hz), 5.26(1H,d, J=11Hz), 5.40(1H,d,J=17Hz), 5.59(1Hs), 5.89– 6.02(1H,m) $IR_{max}^{KBr}$ (cm$^{-1}$): 1780, 1700. $IR_{max}^{KBr}$ (cm$^{-1}$): 1786, 1702 |
| 6 | 60 | NMR (CDCl$_3$)δ: 1.31(3H,d,J=8Hz), 3.66(1H,d, J=6Hz), 4.1–4.2(1H,m), 4.17(2H,q,J=16Hz), 4.66 and 4.80(2H,AB type dd,J=13Hz,5Hz), 5.25(1H,d,J=11Hz), 5.40(1H,d,J=7Hz), 5.54 (1H,s), 5.88–6.02(1H,m), 5.98(1H,d,J=5Hz), 7.11(1H,s), 7.26(1H,m). |

By conducting the same procedure as described in Example 38, there were synthesized the following compounds from the compounds of Reference Examples, Compound Nos. (55) to (60).

REFERENCE EXAMPLE 7

Potassium (1'R, 5R, 6S and 1',S, 5S, 6R)-2-(2''-furanyl)-6-(1'-hydroxyethyl)penem-3-carboxylate (SUN 4194)

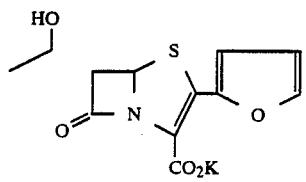

REFERENCE EXAMPLE 8

Potassium (1'R, 5R, 6S and 1'S, 5S, 6R)-2-(3''-furanyl)-6(1'-hydroxyethyl)penem-3-carboxylate (SUN 4196)

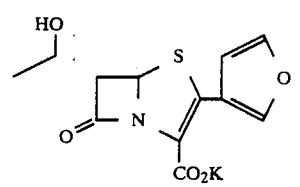

REFERENCE EXAMPLE 9

Potassium (1'R, 5R, 6S and 1'S, 5S, 6R)-6-(1-hydroxyethyl)-2-(methoxymethyl)penem-3-carboxylate (SUN 3585)

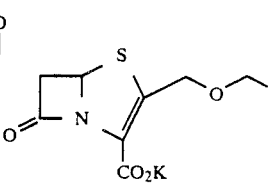

REFERENCE EXAMPLE 10

Potassium (1'R, 5R, 6S and 1's, 5S, 6R)-2-(ethoxymethyl)-6-(1'-hydroxyethyl)-penem-3-carboxylate (SUN 3519)

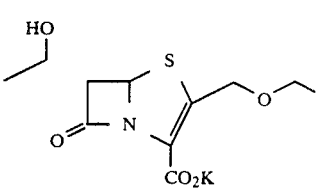

REFERENCE EXAMPLE 11

Potassium (1'R, 5R, 6S and 1'S, 5S, 6R)-2-ethylmethylthio)-6-(1'-hydroxyethyl)-penem-3-carboxylate (SUN 3515)

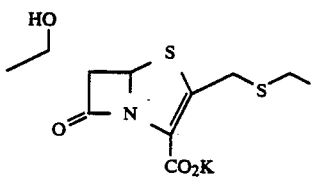

SUN 3515

REFERENCE EXAMPLE 12

Potassium (1'R, 5R, 6S and 1'S, 5S, 6R)-6-(1'-hydroxyethyl)-2-(3"-thiophenemethyl)-penem-3-carboxylate (SUN 3514)

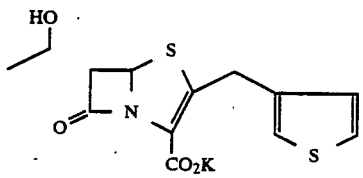

SUN (SUN 3514)

Determination of Minimum Inhibitory Concentrations (MIC)

With regard to the novel compounds obtained according to this invention and the compounds of Reference Examples, their minimum inhibitory concentrations (MIC) were determined by the agar plate dilution method in accordance with the MIC measuring standard method of The Chemotherapeutic Society of Japan, whereby $10^6$ colony forming units were inoculated and the minimal concentration to inhibit the microbial growth after incubation at 37° C. for 18 hours were determined, as shown as μg/ml in Table.

Therapeutic Effect against Experimental Infection of Mice

Out of the novel compounds obtained according to this invention, SUN 4435 was selected to carry out a treatment experiment with infected animals. As an animal, there were employed ICR strain male mice (5-weeks aged, with a body weight of 23 to 27 g), which were inoculated intraperitoneally with S. aureus Smith or E. coli KC-14 and 2 hours later, treated by subcutaneous or oral application of SUN 4435. 5 days thereafter, the mice were observed for survival or death to compare the therapeutic effect.

[Subcutaneous application]

In a group treated through application of 1.6 mg/kg or more of SUN 4435 to mice infected with S. aureus Smith ($5.7 \times 10^5$ colony forming units), every heads were found to survive. With regard to a group treated through application of 2.6 mg/kg or more of SUN 4435 to mice infected with $3.1 \times 10^5$ (colony forming units) of E. coli KC-14, every heads were found to survive, whereas in a group treated through application of 1.5 mg/kg of the same, three mice per five survived.

[Oral application]

In a group treated through application of 9.6 mg/kg or more of SUN 4435 to mice infected with $3.6 \times 10^5$ (CFU/head) of S. aureus Smith, every heads were found to survive, and three heads out of five survived in a group treated through application of 3.9 mg/kg of the same. With reference to a group treated through application of 12.5 mg/kg or more of SUN 4435 to mice infected with $1.5 \times 10^5$ (CFU/head) of E. coli KC-14, every heads were found to survive.

In the case of subcutaneous application, the maximum application rate was 50 mg/kg, while in the event of oral application, the maximum application rate was 70 mg/kg.

| Microorganism | SUN No. | | | | | | | | | |
|---|---|---|---|---|---|---|---|---|---|---|
| | 4068 | 4118 | 4434 | 4435 | 4725 | 4726 | 4740 | 4741 | 4742 | 4770 |
| S. aureus FAD209P JC-1 | 0.1 | 0.1 | 0.05 | 0.05 | 0.05 | 0.05 | 0.1 | 0.1 | 0.05 | 0.2 |
| M. luteus ATCC9341 | 0.1 | 0.05 | <0.025 | 0.05 | 0.1 | 0.05 | 0.05 | 0.1 | 0.1 | 0.1 |
| E. coli NIHI JC-2 | 1.56 | 25 | 6.25 | 0.78 | 1.56 | 1.56 | >50 | 6.25 | 1.56 | 1.56 |
| K. pneumoniae PC1602 | 0.39 | 6.25 | 1.56 | 0.1 | 0.1 | 0.05 | 3.13 | 0.1 | 0.1 | 0.78 |
| Ser. marcescens IMA 1136 | 6.25 | 25 | 25 | 3.13 | 6.25 | 12.5 | >50 | 25 | 6.25 | 50 |
| Pr. morganii IFO3848 | 3.13 | 1 | 6.25 | 6.25 | 12.5 | 12.5 | 25 | 3.13 | 6.25 | 25 |
| Ent. cloacae 963 | 6.25 | 25 | 12.5 | 3.13 | 6.25 | 6.25 | >50 | 25 | 6.25 | 25 |
| Al. fecalis IFO13111 | 1.56 | 1.56 | 3.13 | 0.78 | 1.56 | 1.56 | 6.25 | 0.78 | 0.78 | 6.25 |
| E. coli W3630/Rms212 | 3.13 | 12.5 | 12.5 | 1.56 | 3.13 | 3.13 | >50 | 12.5 | 3.13 | 12.5 |
| E. coli W3630/Rms213 | 3.13 | 12.5 | 6.25 | 0.78 | 1.56 | 1.56 | >50 | 6.25 | 0.78 | 12.5 |
| Pr. vulgaris GN7919 | 0.78 | 1.56 | 0.78 | 0.39 | 0.78 | 1.56 | 1.25 | 3.13 | 0.78 | 6.25 |
| B. fragilis GM7000 | 0.05 | 0.2 | 9.1 | <0.025 | 0.05 | 0.05 | 0.78 | 0.1 | 0.05 | 0.39 |
| B. fragilis V-280-1 | 0.2 | 0.2 | 0.2 | 0.2 | 0.05 | 0.05 | 0.78 | 0.1 | 0.05 | 0.39 |
| F. varium ATCC8501 | 0.78 | 1.56 | 1.56 | 0.2 | 0.39 | 0.1 | 6.25 | 0.39 | 0.78 | 3.13 |
| | 4771 | 4262 | 4374 | 4325 | 3514 | 4194 | 4196 | 3585 | 3519 | 3515 |
| S. aureus FAD209P JC-1 | 0.05 | 0.2 | 0.1 | 3.13 | 0.05 | 0.39 | 0.2 | 0.1 | 0.2 | 0.1 |
| M. luteus ATCC9341 | 0.1 | 0.2 | 0.1 | 1.56 | 0.2 | 0.2 | 0.2 | 0.1 | 0.2 | 0.2 |
| E. coli NIHI IC-2 | 1.56 | 3.13 | 1.56 | 25 | >50 | 25 | 1.25 | 0.78 | 6.25 | 25 |
| K. pneumoniae PC1602 | 0.05 | 1.56 | 0.39 | 1.25 | 0.78 | 3.13 | 3.13 | 0.78 | 1.56 | 0.78 |
| Ser. marcescens IMA1136 | 6.25 | 12.5 | 3.13 | 50 | 50 | 25 | 25 | 3.13 | 12.5 | 25 |
| Pr. morganii IFO3848 | 6.25 | 12.5 | 3.13 | 50 | 8.13 | 12.5 | 12.5 | 6.25 | 6.25 | 3.13 |
| Ent. cloacae 963 | 3.13 | 12.5 | 3.13 | >50 | >50 | 25 | 25 | 3.13 | 12.5 | 50 |
| Al. fecalis IFO13111 | 0.78 | 3.13 | 1.56 | 12.5 | 0.39 | 6.25 | 12.5 | 1.56 | 1.56 | 0.78 |
| E. coli W3630/Rms212 | 1.56 | 3.13 | 1.56 | >50 | 50 | 25 | 25 | 0.78 | 6.25 | 25 |
| E. coli W3630/Rms213 | 0.73 | 3.13 | 0.78 | 25 | 25 | 25 | 25 | 0.78 | 6.25 | 12.5 |
| Pr. vulgaris GN7919 | 0.78 | 3.13 | 0.78 | >50 | 6.25 | 3.13 | 3.13 | 0.78 | 1.56 | 1.56 |
| B. fragilis GM7000 | 0.025 | 0.2 | | 3.13 | 0.39 | 0.39 | 0.78 | 0.05 | 0.1 | 0.1 |
| B. fragilis V-280-1 | 0.05 | 0.2 | >12.5 | | 0.39 | 6.25 | 12.5 | 0.1 | 0.1 | 0.2 |

| | -continued | | | | | | | | |
|---|---|---|---|---|---|---|---|---|---|
| Microorganism | SUN No. | | | | | | | | |
| F. varium ATCC8501 | 0.78 | 3.13 | >12.5 | 0.39 | 6.25 | 6.25 | 0.78 | 0.39 | 0.39 |

Therapeutic Effect against Experimental Infection in Mice

Out of the novel compound obtained according to this invention, SUN 4435 was selected to carry out a treatment experiment with infected animals. As an animal, there were employed ICR strain male mice (5-weeks aged, with an average body weight of 29.1 g), which were infected intraperitoneally with a test microorganism, S. aureus Smith or E. coli KC-14, and 24 hours later, treated by subcutaneous or oral application of SUN 4435 or SUN 5555. $ED_{50}$ values were determined from the survival rates found after 6 days in accordance with the Probit method.

| | Application method | | |
|---|---|---|---|
| | Subcutaneous | Oral | |
| Test | Comp.'d. No. | | |
| microorganism | SUN 4435 | SUN 4435 | SUN 5555 |
| S. aureus Smith | 1.6 to 1.0 | 5.9 | 5.6 |
| E. coli KC-14 | 1.5 | 11.0 | 13.9 |
| | (Unit: mg/kg) | | |

Acute Toxicity Test

Out of the novel compounds obtained according to this invention, SUN 4435 and SUN 5555 were selected to carry out an acute toxicity test. As an animal, there were employed ICR strain mice (4-weeks aged), which were treated by oral and intravenous application of the compounds. In the case of intravenous application, every of two male and female mice, which received SUN 5555 at a rate of 3 g/kg, survived, while one out of five male mice receiving 5 g/kg of the compound was found to survive.

With regard to SUN 4435, the 50% lethal doses ($LD_{50}$) were determined using groups consisting each of six male and female mice, with the result that the values were found to be 480 mg/kg for male mice and 455.5 mg/kg for female mice.

In the case of oral application, both male and female mice, which received SUN 4435 and SUN 5555 respectively at a rate of 5 g/kg, were found to survive.

Distribution of Sensitivity toward Clinically Isolated Microbial Strains

With regard to the novel compound, SUN 5555, as obtained according to this invention, sensitivities were determined toward the S. aureus strain 87, E. coli strain 88, Klebsiella sp. strain 63, P. mirabillis strain 30, P. vulgaris strain 41, M. morganii strain 29, P. rettgeri strain 17, S. marcescens strain 88, A. calcoaceticus strain 57 and H. influenza strain 25. The determinations were carried out in accordance with the minimal growth inhibitory concentration measuring method as specified by The Chemotherapeutic Society of Japan, with the results being shown in Table in terms of the concentration in the unit of μg/ml to inhibit the 50% and 80% growth of the test microorganisms and strains, respectively.

| Test microorganism | $MIC_{50}$ | $MIC_{90}$ |
|---|---|---|
| S. aureus | 0.1 | 0.2 |
| Methycillin-resistant | | |
| S. aureus | 1.56 | >100 |
| S. pyogenenes | <0.025 | <0.025 |
| E. coli | 0.78 | 1.56 |
| Klebsiella sp. | 0.78 | 1.56 |
| P. mirabillis | 3.13 | 6.25 |
| P. vulgaris | 3.13 | 6.25 |
| M. morganii | 1.56 | 6.25 |
| P. rettgeri | 1.56 | 6.25 |
| S. marcescens | 1.56 | 6.25 |
| A. calcoaceticus | 6.25 | 25 |
| H. influenza | 0.39 | 0.78 |

We claim:

1. A penem compound represented by the formula:

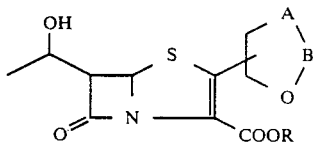

(wherein R denotes hydrogen or allyl group, A denotes oxygen atom or methylene group and B denotes methylene, ethylene or carbonyl group) or a pharmacologically acceptable salt thereof.

2. A compound as claimed in claim 1 wherein R is hydrogen atom or allyl group and —COOR is a carboxyl group in the form of sodium, potassium or calcium salt.

3. A compound as claimed in claim 1 wherein

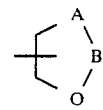

is tetrahydrofuryl group.

4. A compound as claimed in claim 1 wherein

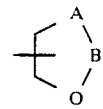

is tetrahydropyranyl group.

5. A compound as claimed in claim 1 wherein

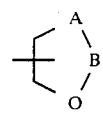

is 1,4-dioxanyl group.

6. A compound as claimed in claim 1 wherein

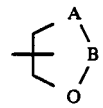

is 5-oxo-oxoranyl group.

7. A compound as claimed in claim 1 wherein the compound is an optically active compound.

8. A compound as claimed in claim 1 wherein the carbon atom attached by hydroxyl group in hydroxyethyl group at 6-position of the penem ring has R configuration and the steric configuration of 5R, 6S in the penem ring.

9. A pharmaceutical composition useful as an antibiotic agent which comprises an antibacterial effective amount of a penem compound having the general formula:

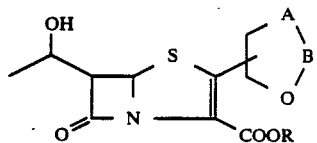

wherein R denotes hydrogen or an allyl group, A denotes oxygen or methylene, and B denotes a methylene, ethylene or carbonyl group and a pharmaceutically acceptable carrier therefor.

10. A pharmaceutical composition as claimed in claim 9 which contains the penem compound in a daily dose of 50 mg to 5 g.

11. The penem compound of claim 1, which is

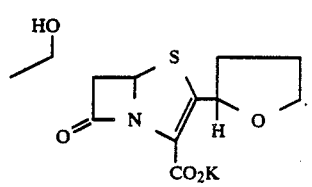

12. The penem compound of claim 1, which is

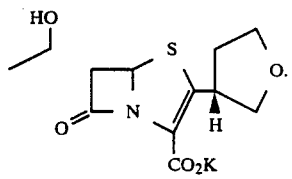

13. The penem compound of claim 1, which is

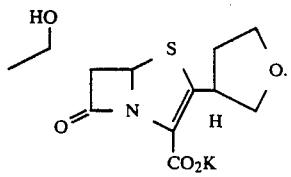

14. The pharmaceutical composition of claim 9, wherein the penem compound is

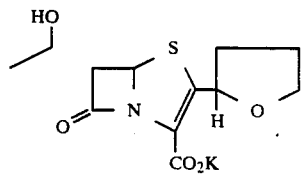

15. The pharmaceutical composition of claim 9, wherein the penem compound is

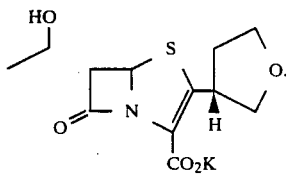

16. The pharmaceutical composition of claim 9, wherein the penem compound is

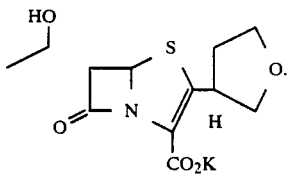

* * * * *

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 3, line 20; formula (5) should read as follows:

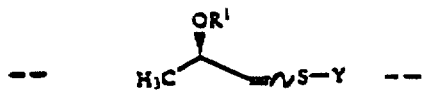

Column 3, line 55; formulas (2a) and (2b) should read as follows:

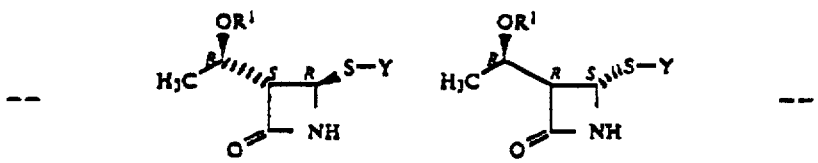

Column 4, line 25: "thiocarbonic" should read --thiocarboxylic--

Column 4, line 55: " P(Z)₃ " should read
　　　　　　　　　　　　Process 3

-- P9Z)₃ --
　Process 4

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 4, line 65; formula (14) should read as follows:

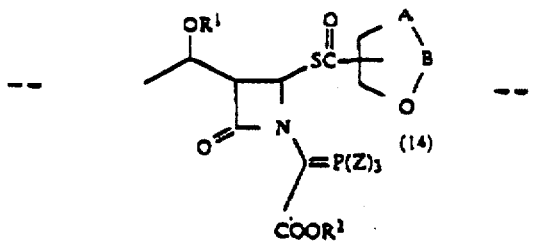

Column 5, lines 30, 40 and 50; that part of formulas 18, 17 and 1 reading:

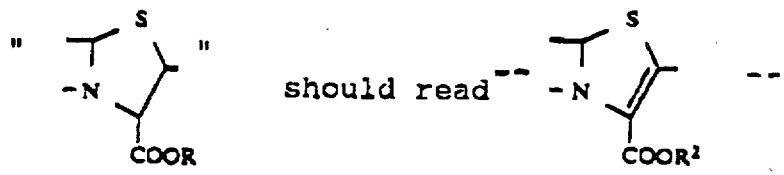

Column 10, line 48: "exhisibits" should read --exhibits--

Column 10, line 48, 55 and 62: "antibial" should read --antibacterial--

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

| At | Column | Line | Formula |
|---|---|---|---|
| | 12 | 40 | 1 |
| | 12 | 50 | 2 |
| | 13 | 25 | 3 |
| | 13 | 35 | 4 |
| | 14 | 5 | 3 |
| | 15 | 20 | 7 |
| | 15 | 30 | 5 |
| | 16 | 15 | 2 |
| | 16 | 40 | 10 |
| | 17 | 55 | 4 |
| | 20 | 10 | 21 |
| | 20 | 20 | 22 |
| | 20 | 45 | 21 |
| | 20 | 55 | 23 |
| | 21 | 10 | 21 |

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

| At | Column | Line | Formula |
|---|---|---|---|
| | 21 | 20 | 24 |
| | 21 | 55 | 25 |
| | 22 | 10 | 11 |
| | 23 | 25 | 20 |
| | 23 | 35 | 28 |
| | 24 | 30 | 14 |
| | 24 | 40 | 30 |
| | 25 | 15 | 17 |
| | 25 | 25 | 30 |
| | 25 | 50 | 20 |
| | 25 | 60 | 31 |
| | 26 | 15 | 22 |
| | 26 | 25 | 32 |
| | 26 | 60 | 23 |
| | 27 | 45 | 24 |

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

| At | Column | Line | Formula |
|---|---|---|---|
|  | 27 | 55 | 36 |
|  | 28 | 15 | 36 |
|  | 31 | 45 | 32 |
|  | 32 | 45 | 34 |
|  | 33 | 45 | 36 |
|  | 34 | 10 | 37 |

At each occurrence, that portion of the formula reading:

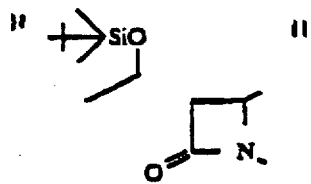 should read 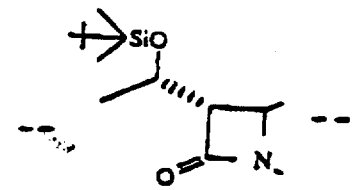

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

Page 6 of 33

It is certified that error appears in the above-identified patent and that said Letters Patent is hereby corrected as shown below:

| At | Column | Line | Formula |
|----|--------|------|---------|
|    | 31 | 55 | 43 |
|    | 32 | 55 | 45 |
|    | 33 | 55 | 47 |
|    | 34 | 20 | 48 |
|    | 36 | 20 | 52 |
|    | 39 | 40 | 52 |
|    | 39 | 50 | - |
|    | 39 | 55 | - |
|    | 40 | 65 | 42 |
|    | 41 | 5  | - |
|    | 41 | 30 | 45 |
|    | 41 | 35 | - |
|    | 42 | 30 | 58 |
|    | 42 | 37 | - |
|    | 43 | 65 | 41 |

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

| At | Column | Line | Formula |
|---|---|---|---|
| | 44 | 5 | - |
| | 45 | 5 | 48 |
| | 45 | 15 | - |
| | 45 | 40 | 44 |
| | 45 | 48 | - |
| | 46 | 5 | 47 |
| | 46 | 15 | - |
| | 46 | 43 | 48 |
| | 46 | 50 | - |
| | 49 | 30 | - |
| | 49 | 45 | - |
| | 49 | 55 | 57 |
| | 50 | 23 | 58 |
| | 50 | 38 | 59 |
| | 50 | 50 | 60 |

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

| At | Column | Line | Formula |
|----|--------|------|---------|
|    | 51     | 50   | -       |
|    | 51     | 65   | -       |
|    | 52     | 50   | -       |
|    | 52     | 65   | -       |
|    | 53     | 10   | -       |
|    | 53     | 25   | -       |
|    | 57     | 47   | -       |
|    | 58     | 5    | -       |
|    | 58     | 25   | -       |
|    | 58     | 35   | -       |

At each occurrence, that portion of the formula reading:

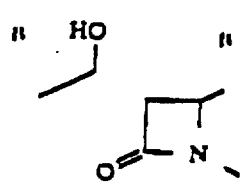 should read 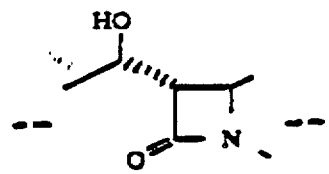

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 14, line 15; formula 5 should read as follows:

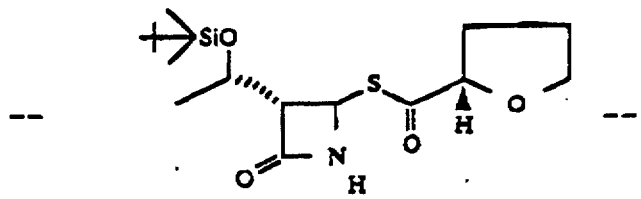

Column 14, line 20; column 15, line 38 and column 19, line 30; at each occurrence formula 6 should read as follows:

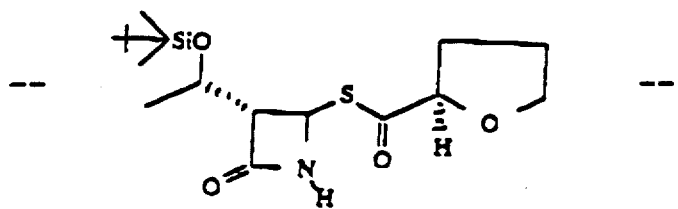

Column 16, line 22; formula 8 should read as follows:

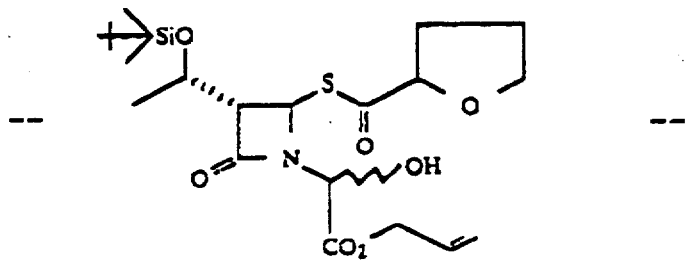

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 16, line 30; formula 9 should read as follows:

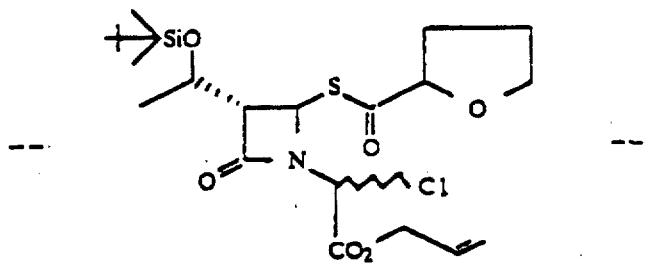

Column 17, line 20, formulas 11 and 10 at each occurrence, that portion of the formula reading:

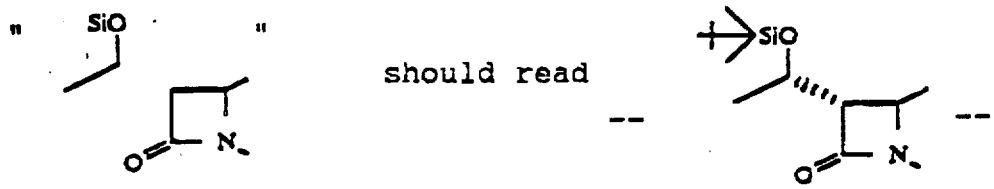

Column 17, line 28 and column 23, line 41: "(1'R," should read --(1"R,--

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 17, line 26; formula 12 should read as follows:

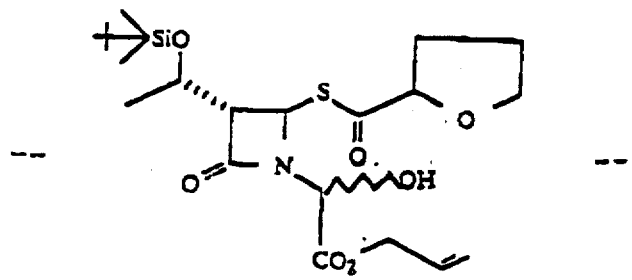

Column 18, line 5; formula 13 should read as follows:

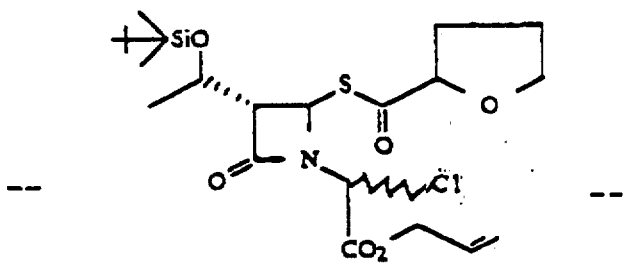

Column 18, line 15; formula 14 should read as follows:

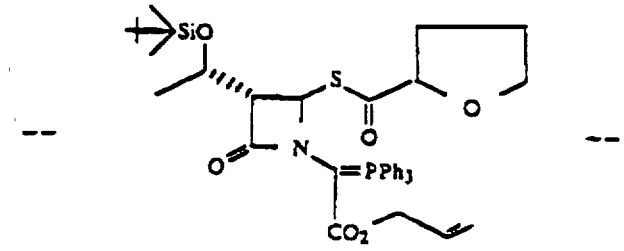

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 18, line 45; formula 5 should read as follows:

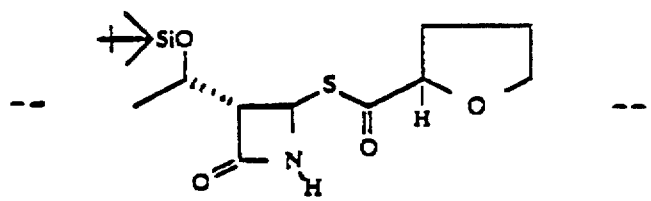

Column 18, line 55; formula 15 should read as follows:

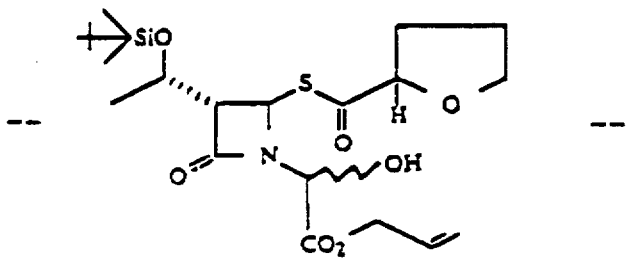

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 18, line 65; formula 16 should read as follows:

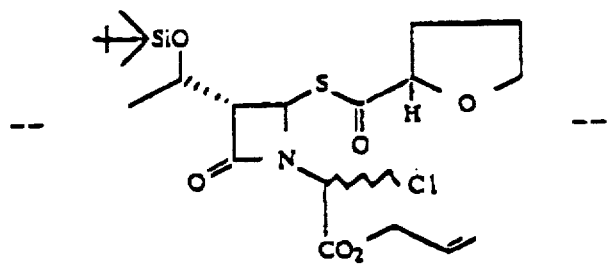

Column 19, line 5, that portion of the formula reading:

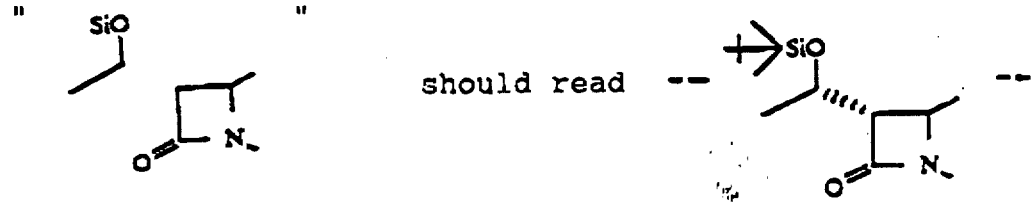

Column 19, line 40; formula 18 should read as follows:

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

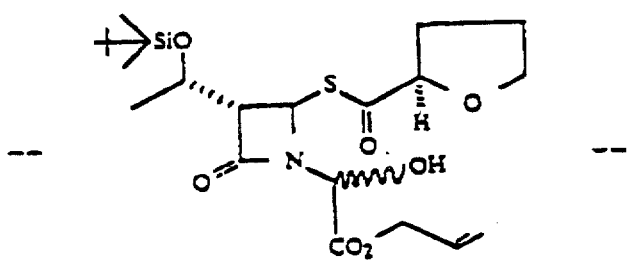

Column 19, line 50; formula 19 should read as follows:

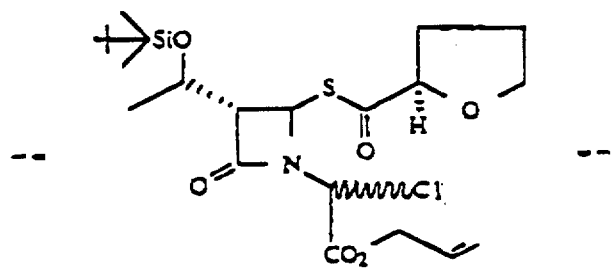

Column 19, line 55; formula 20 should read as follows:

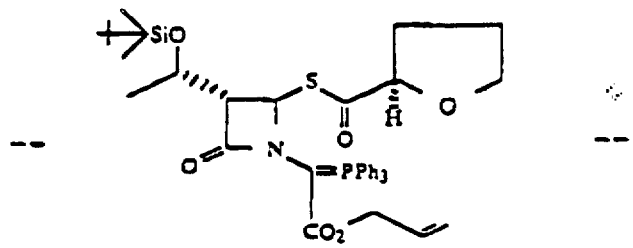

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 21, line 45; formula 11 should read as follows:

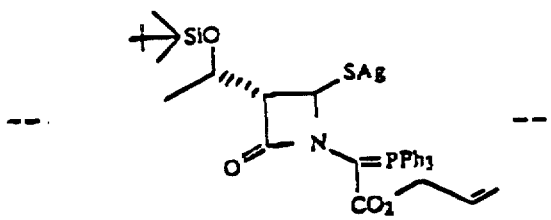

Column 22, line 12

Column 23, line 26, and line 63

Column 25, line 15

Column 31, line 12

Column 43, line 63

Column 45, line 5 and line 40

Column 46, line 5 and line 43

Column 47, line 10 at each occurrence, to the right of the formula insert -- ⟶ --

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

Column 22, line 20 and column 28, line 63; formula 26 should read as follows:

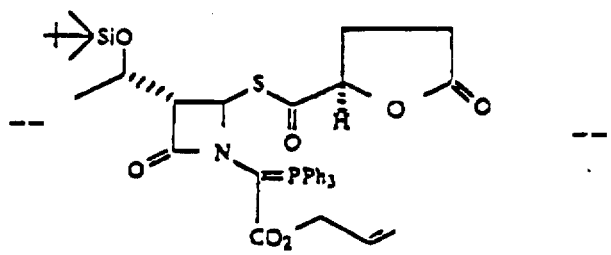

Column 22, line 45; formula 10 should read as follows:

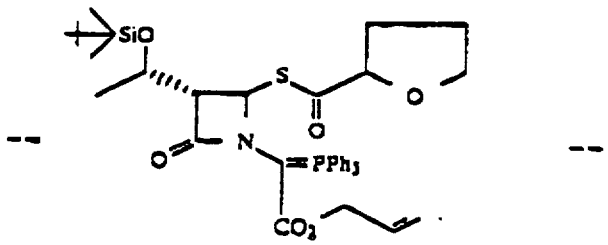

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 22, line 55 and column 36, line 12; formula 27 should read as follows:

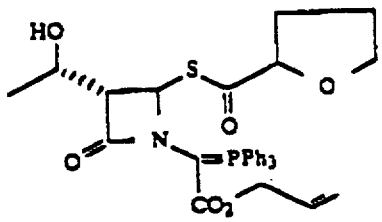

Column 22, line 68: "bromide" should read --fluoride--

Column 23, line 63; formula 25 should read as follows:

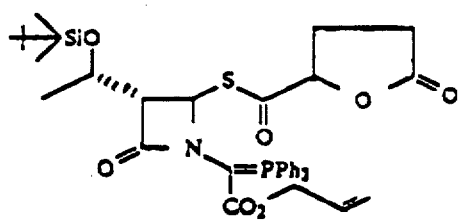

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 24, line 5 and column 37, line 10; formula 29 should read as follows:

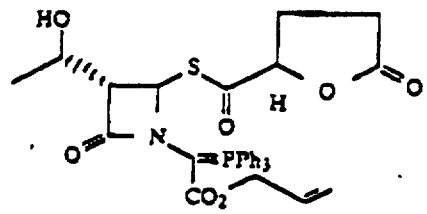

Column 25, line 30: "2S'''S," should read --2'''S,--

Column 25, line 50; formula 20 should read as follows:

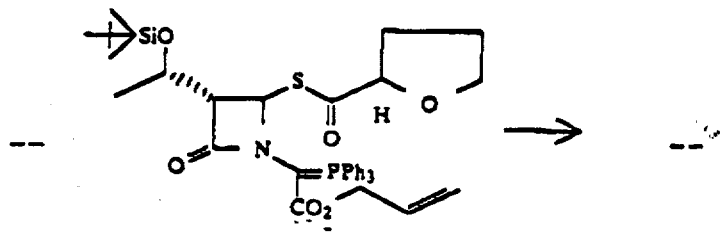

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 25, line 60 and column 31, line 12: the formula should read as follows:

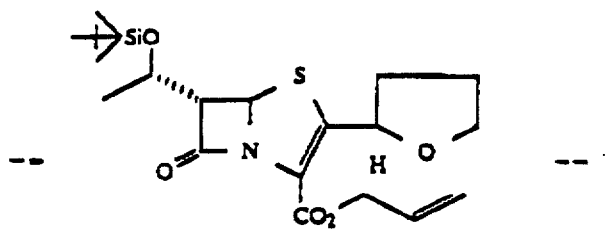

Column 26, line 35 and column 32, line 11; formula 33 should read as follows:

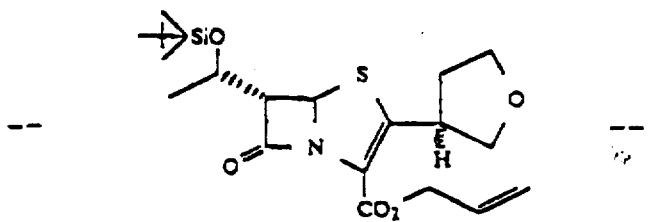

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

Column 27, line 5; formula 34 should read as follows:

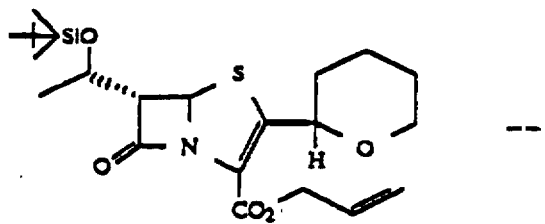

Column 27, line 15 and column 33, line 13; formula 35 should read as follows:

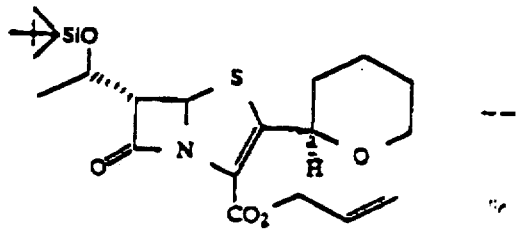

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 28, line 22; formula 37 should read as follows:

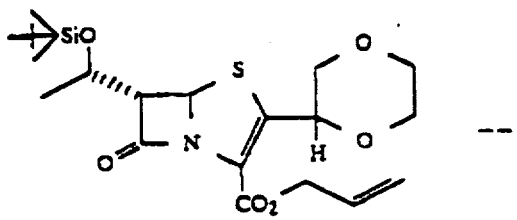

Column 28, line 35 and column 34, line 45; formula 38 should read as follows:

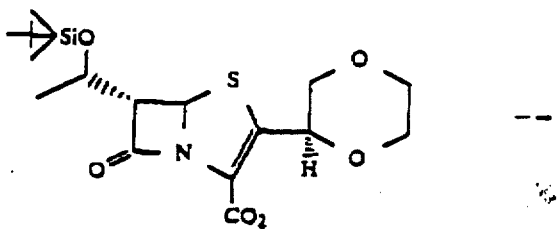

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

Column 29, line 5 and column 35, line 15; formula 39 should read as follows:

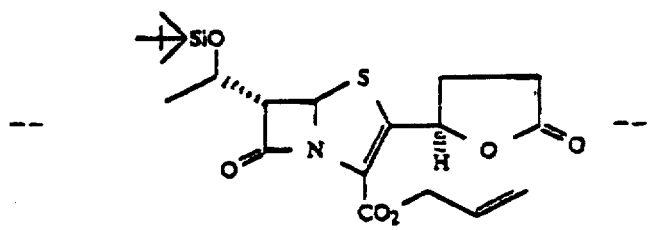

Column 29, line 15 and column 35 line 48; formula 40 should read as follows:

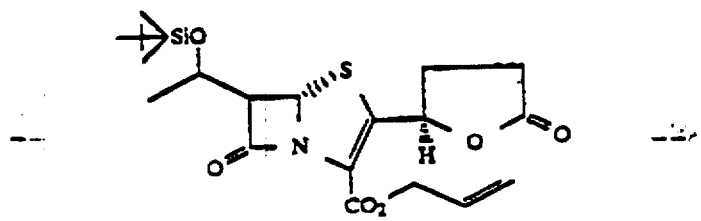

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 30, line 48; the formula should read as follows:

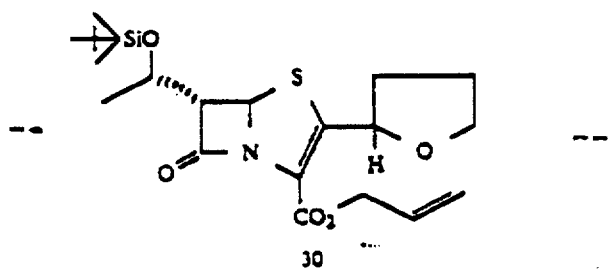

Column 30, line 56; the formula should read as follows:

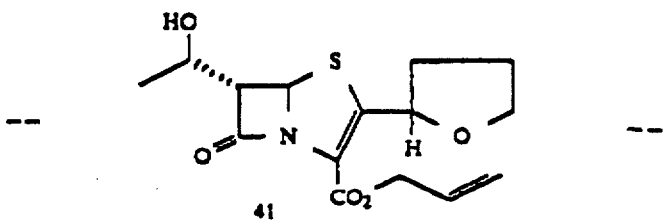

Column 31, line 16: below the formula insert "31"

Column 31 line 20, column 36 line 55, column 40, line 30, and column 44 line 42; the formula should read as follows:

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

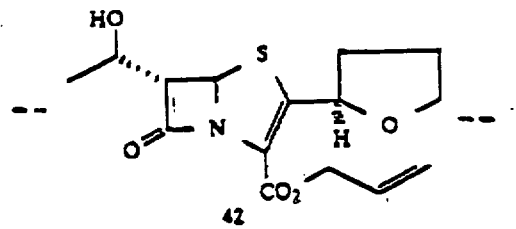

Column 32, line 20; formula 44 should read as follows:

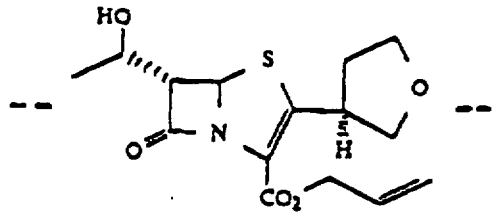

Column 33, line 20 and column 41, line 65; formula 46 should read as follows:

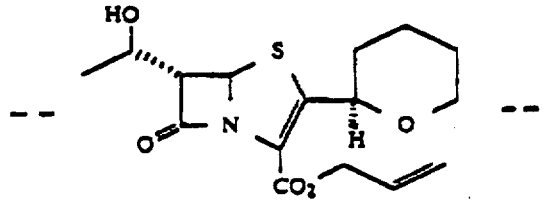

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 34, line 55 and column 47, line 10; formula 49 should read as follows:

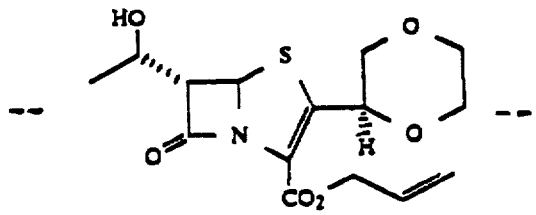

Column 35, line 20 and column 42, line 63; formula 50 should read as follows:

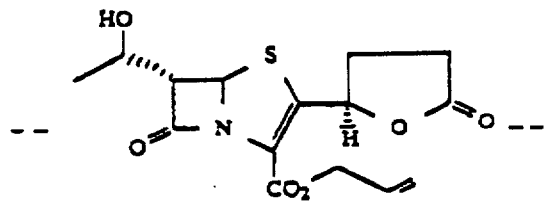

Column 35, line 55 and column 43, line 30; formula 51 should read as follows:

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

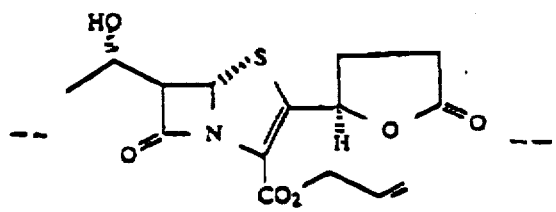

Column 36, line 45; formula 28 should read as follows:

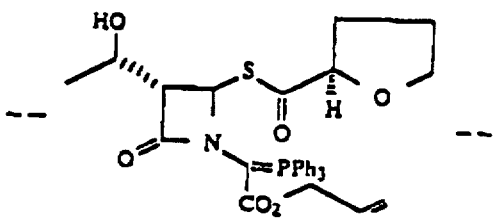

Column 37, line 10; formula 29 should read as follows:

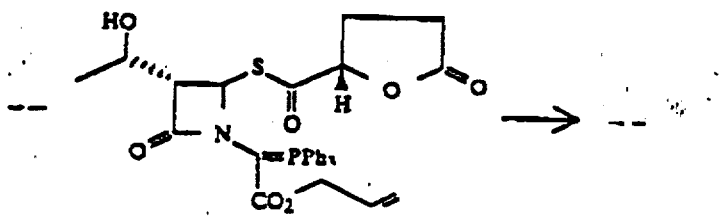

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 37, line 20; formula 53 should read as follows:

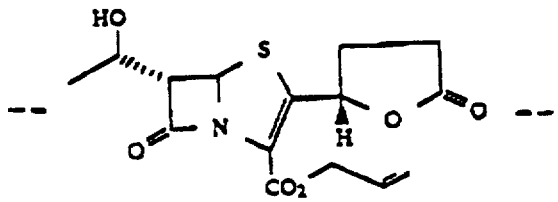

Column 37, line 41; formula 54 should read as follows:

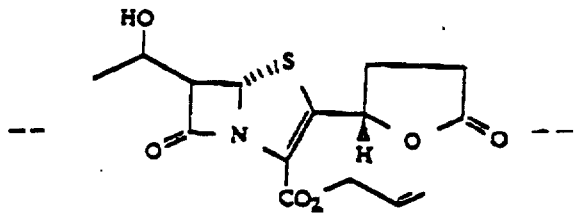

Column 39, line 36: "phenem-8-carboxylate" should read --phenem-3-carboxylate--

Column 39, line 68

Column 40, lines 47 and 48

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

Column 41, lines 14 and 15; lines 46 and 47

Column 42, lines 14 and 15; lines 46 and 47

Column 43, lines 14 and 15; lines 48 and 49

Column 44, lines 14 and 15; line 59

Column 45, line 23; line 57

Column 46, lines 25 and 26; line 62

Column 48, line 13

"palladium tetrakis-triphenylphosphine" should read --tetrakis (triphenylphosphine) palladium--

Column 40, line 40; the formula should read as follows:

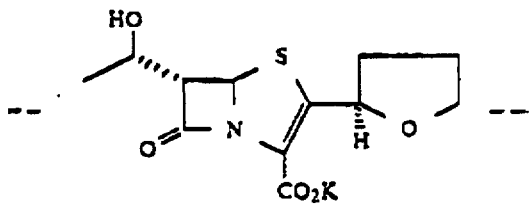

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 42, line 5; the formula should read as follows:

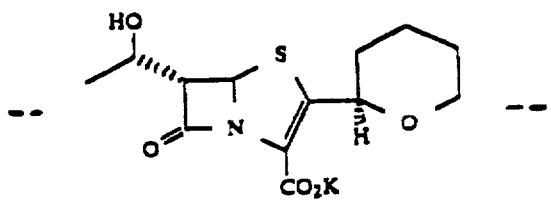

Column 43, line 5; the formula should read as follows:

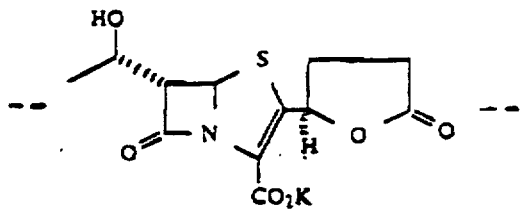

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 43, line 40; the formula should read as follows:

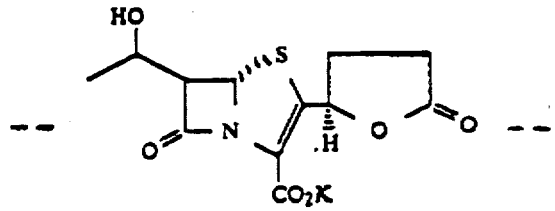

Column 44, line 50; the formula should read as follows:

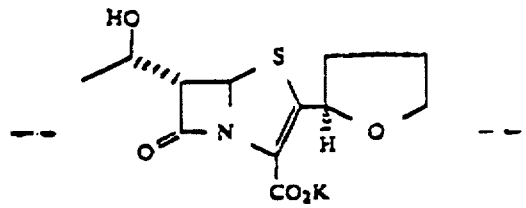

Column 45, line 66: "paradioxanyl" should read --para-dioxanyl--

UNITED STATES PATENT AND TRADEMARK OFFICE
CERTIFICATE OF CORRECTION

PATENT NO. : 4,997,829
DATED : March 5, 1991
INVENTOR(S) : Ishiguro, et al

It is certified that error appears in the above-identified patent and that said Letters Patent is hereby corrected as shown below:

Column 48, line 5; the formula should read as follows:

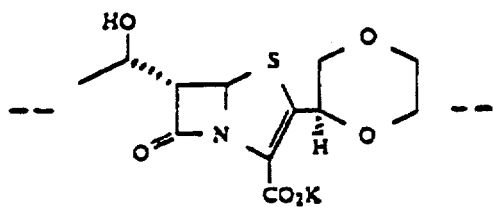

Column 58, line 15 and column 58, line 48; the formula should read as follows:

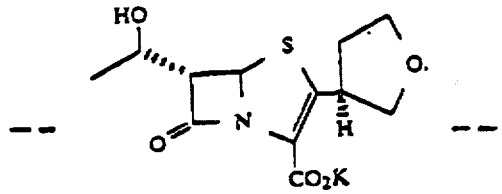

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al

It is certified that error appears in the above-identified patent and that said Letters Patent is hereby corrected as shown below:

| Column | Line | Below the Formula insert |
|---|---|---|
| 49 | 34 | 55 |
|    | 48 | 56 |
|    | 61 | 57 |
| 50 | 29 | 58 |
|    | 42 | 59 |
|    | 56 | 60 |
| 51 | 54 | SUN 4194 |
|    | 67 | SUN 4196 |
| 52 | 54 | SUN 3585 |
|    | 67 | SUN 3519 |

UNITED STATES PATENT AND TRADEMARK OFFICE
CERTIFICATE OF CORRECTION

PATENT NO. : 4,997,829

DATED : March 5, 1991

INVENTOR(S) : Ishiguro, et al.

Page 33 of 33

It is certified that error appears in the above-indentified patent and that said Letters Patent is hereby corrected as shown below:

53         14        SUN 3515

28        SUN 3514

Signed and Sealed this

Thirtieth Day of May, 1995

Attest:

*Attesting Officer*

BRUCE LEHMAN

*Commissioner of Patents and Trademarks*